(12) United States Patent
Tachon et al.

(10) Patent No.: US 11,266,584 B2
(45) Date of Patent: *Mar. 8, 2022

(54) COSMETIC COMPOSITION COMPRISING COMPOSITE SUNSCREEN PARTICLES

(75) Inventors: Romain Tachon, Kawasaki (JP); Momoko Shimizu, Kanagawa (JP); Shinichi Matsufuji, Kanagawa (JP)

(73) Assignee: L'OREAL, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 14/412,773

(22) PCT Filed: Jul. 13, 2012

(86) PCT No.: PCT/JP2012/068526
§ 371 (c)(1),
(2), (4) Date: Jan. 5, 2015

(87) PCT Pub. No.: WO2014/010100
PCT Pub. Date: Jan. 16, 2014

(65) Prior Publication Data
US 2015/0190320 A1    Jul. 9, 2015

(51) Int. Cl.
| | | |
|---|---|---|
| *A61K 8/29* | (2006.01) | |
| *A61Q 17/04* | (2006.01) | |
| *A61K 8/81* | (2006.01) | |
| *A61K 8/02* | (2006.01) | |
| *A61K 8/89* | (2006.01) | |

(52) U.S. Cl.
CPC .............. *A61K 8/29* (2013.01); *A61K 8/0241* (2013.01); *A61K 8/0279* (2013.01); *A61K 8/8117* (2013.01); *A61K 8/8147* (2013.01); *A61K 8/8152* (2013.01); *A61K 8/89* (2013.01); *A61Q 17/04* (2013.01); *A61K 2800/612* (2013.01)

(58) Field of Classification Search
None
See application file for complete search history.

(56) References Cited

U.S. PATENT DOCUMENTS

| | | | |
|---|---|---|---|
| 2,104,492 A | 1/1938 | Merkel et al. | |
| 2,463,264 A | 3/1949 | Graenacher et al. | |
| 2,995,540 A | 8/1961 | Duennenberger et al. | |
| 3,709,437 A | 1/1973 | Wright | |
| 3,937,364 A | 2/1976 | Wright | |
| 4,022,351 A | 5/1977 | Wright | |
| 4,077,441 A | 3/1978 | Rosen et al. | |
| 4,147,306 A | 4/1979 | Bennett | |
| 4,184,615 A | 1/1980 | Wright | |
| 4,184,625 A | 1/1980 | Johnson et al. | |
| 4,217,344 A | 8/1980 | Vanlerberghe et al. | |
| 4,246,257 A * | 1/1981 | Elliott ...................... | A61K 8/06 424/69 |
| 4,247,411 A | 1/1981 | Vanlerberghe et al. | |
| 4,293,543 A | 10/1981 | Cotte et al. | |
| 4,585,597 A | 4/1986 | Lang et al. | |
| 4,588,839 A | 5/1986 | Lang et al. | |
| 4,598,862 A | 7/1986 | Rice | |
| 4,615,467 A | 10/1986 | Grogan et al. | |
| 4,617,390 A | 10/1986 | Hoppe et al. | |
| 4,699,779 A | 10/1987 | Palinczar | |
| 4,772,471 A | 9/1988 | Vanlerberghe et al. | |
| 4,797,493 A | 1/1989 | Matsuno et al. | |
| 4,814,162 A | 3/1989 | Lang et al. | |
| 4,850,517 A | 7/1989 | Ter Stege | |
| 4,897,308 A | 1/1990 | Vanlerberghe et al. | |
| 4,985,237 A | 1/1991 | Matsuno et al. | |
| 5,000,945 A | 3/1991 | Kobayashi et al. | |
| 5,021,200 A | 6/1991 | Vanlerberghe et al. | |
| 5,030,446 A * | 7/1991 | Russ ........................ | A61K 8/11 424/63 |
| 5,030,466 A | 7/1991 | Kageyama et al. | |
| 5,064,641 A | 11/1991 | Lang et al. | |
| 5,087,729 A | 2/1992 | Matsuno et al. | |
| 5,166,355 A | 11/1992 | Leistner et al. | |
| 5,205,837 A | 4/1993 | Andrean et al. | |
| 5,217,709 A | 6/1993 | Lagrange et al. | |
| 5,223,533 A | 6/1993 | Forestier et al. | |

(Continued)

FOREIGN PATENT DOCUMENTS

| | | |
|---|---|---|
| CH | 350763 A | 12/1960 |
| CN | 101695466 A | 4/2010 |

(Continued)

OTHER PUBLICATIONS

JP2007254429 Machine Translation, 2007.*
Shin-Etsu Technical Data Sheet, KSG-16, http:/www.silicone.jp/e/, 2012.*
Shin-Etsu Technical Data Sheet, KSG-15, http:/www.silicone.jp/e/, 2012.*
International Search Report for PCT/JP2012/068526 (dated May 2, 2013).
English language abstract for FR 2868694 (Oct. 14, 2005).

(Continued)

*Primary Examiner* — Jennifer A Berrios
(74) *Attorney, Agent, or Firm* — The Marbury Law Group, PLLC

(57) ABSTRACT

The present invention relates to a cosmetic composition comprising, at least: (i) at least one composite pigment comprising at least one small particle with a mean particle size of more than 100 nm and less than 1 μm, preferably less than 600 nm, and more preferably less than 400 nm, wherein the surface of the small particle is at least in part covered with at least one coating layer comprising at least one inorganic or organic particulate solid UV filter; (ii) at least one organopolysiloxane elastomer; and (iii) at least one oil absorbing agent with oil absorption capability of 1 ml/1 g or more in an amount of more than 1% by weight relative to the total weight of composition.

15 Claims, 1 Drawing Sheet

(56) References Cited

U.S. PATENT DOCUMENTS

| | | | |
|---|---|---|---|
| 5,236,986 A | 8/1993 | Sakuta | |
| 5,237,071 A | 8/1993 | Leistner et al. | |
| 5,240,975 A | 8/1993 | Winter et al. | |
| 5,346,693 A | 9/1994 | Pilleux et al. | |
| 5,362,881 A | 11/1994 | Leistner et al. | |
| 5,364,031 A | 11/1994 | Taniguchi et al. | |
| 5,373,037 A | 12/1994 | Leistner et al. | |
| 5,399,563 A | 3/1995 | Stein et al. | |
| 5,412,004 A | 5/1995 | Tachibana et al. | |
| 5,501,850 A | 3/1996 | Stein et al. | |
| 5,505,935 A * | 4/1996 | Guerrero | A61K 8/37 424/59 |
| 5,512,094 A | 4/1996 | Linton | |
| 5,518,713 A | 5/1996 | Raspanti | |
| 5,538,793 A | 7/1996 | Inokuchi et al. | |
| 5,585,091 A | 12/1996 | Pelzer et al. | |
| 5,643,864 A | 7/1997 | Li et al. | |
| 5,656,586 A | 8/1997 | Li et al. | |
| 5,677,314 A | 10/1997 | Stein et al. | |
| 5,687,521 A | 11/1997 | Carlson et al. | |
| 5,688,995 A | 11/1997 | Luther et al. | |
| 5,705,169 A | 1/1998 | Stein et al. | |
| 5,714,457 A | 2/1998 | Kitsuki et al. | |
| 5,730,960 A | 3/1998 | Stein et al. | |
| 5,783,554 A | 7/1998 | Li et al. | |
| 5,798,331 A | 8/1998 | Anderson et al. | |
| 5,811,487 A | 9/1998 | Schulz, Jr. | |
| 5,837,793 A | 11/1998 | Harashima et al. | |
| 5,846,310 A | 12/1998 | Noguchi et al. | |
| 5,849,909 A | 12/1998 | Richard et al. | |
| 5,863,886 A | 1/1999 | Tracy et al. | |
| 5,872,149 A | 2/1999 | Dralle-Voss et al. | |
| 5,888,481 A | 3/1999 | Horn et al. | |
| 5,914,310 A | 6/1999 | Li et al. | |
| 5,928,630 A | 7/1999 | Richard et al. | |
| 5,958,382 A | 9/1999 | Vidal et al. | |
| 5,958,431 A | 9/1999 | Brancq et al. | |
| 5,961,960 A | 10/1999 | Dilk et al. | |
| 6,004,540 A | 12/1999 | Richard et al. | |
| 6,007,796 A | 12/1999 | Menzel et al. | |
| 6,030,939 A | 2/2000 | Gruning | |
| 6,034,271 A | 3/2000 | Kwetkat | |
| 6,086,666 A | 7/2000 | Noguchi et al. | |
| 6,121,482 A | 9/2000 | Kwetkat et al. | |
| 6,156,721 A | 12/2000 | Kwetkat et al. | |
| 6,159,455 A | 12/2000 | Habeck et al. | |
| 6,225,467 B1 | 5/2001 | Esteghamatian et al. | |
| 6,235,270 B1 * | 5/2001 | Ishii | A61K 8/11 106/403 |
| 6,306,376 B1 | 10/2001 | Philippe | |
| 6,322,775 B1 | 11/2001 | Malle et al. | |
| 6,342,625 B1 | 1/2002 | Kwetkat et al. | |
| 6,365,135 B1 | 4/2002 | Philippe et al. | |
| 6,376,679 B2 | 4/2002 | Leduc et al. | |
| 6,423,854 B1 | 7/2002 | Philippe et al. | |
| 6,432,535 B1 | 8/2002 | Noguchi et al. | |
| 6,482,441 B1 | 11/2002 | Hasegawa et al. | |
| 6,514,486 B1 | 2/2003 | Tuloup et al. | |
| 6,585,983 B1 | 7/2003 | Heinrich et al. | |
| 6,645,476 B1 | 11/2003 | Morschhauser et al. | |
| 6,710,022 B1 | 3/2004 | Kwetkat et al. | |
| 6,710,091 B1 * | 3/2004 | Womelsdorf | B82Y 5/00 423/101 |
| 7,311,897 B2 | 12/2007 | Ehlis et al. | |
| 7,393,817 B2 | 7/2008 | Kwetkat et al. | |
| 8,083,264 B2 | 12/2011 | Iftime et al. | |
| 9,913,782 B2 | 3/2018 | Nagamatsu et al. | |
| 2001/0028890 A1 | 10/2001 | Miyazaki et al. | |
| 2001/0031272 A1 | 10/2001 | Noguchi et al. | |
| 2001/0053856 A1 | 12/2001 | Leduc et al. | |
| 2002/0005145 A1 | 1/2002 | Sherman | |
| 2002/0010179 A1 | 1/2002 | Richard et al. | |
| 2003/0101908 A1 | 6/2003 | Hayashi et al. | |
| 2003/0105213 A1 | 6/2003 | Hayashi et al. | |
| 2003/0215474 A1 | 11/2003 | Miyazaki et al. | |
| 2004/0176266 A1 | 9/2004 | Kwetkat et al. | |
| 2004/0191191 A1 | 9/2004 | Ehlis et al. | |
| 2005/0031653 A1 | 2/2005 | Kwekat et al. | |
| 2005/0163730 A1 * | 7/2005 | Rosevear et al. | 424/59 |
| 2005/0238979 A1 | 10/2005 | Dumousseaux | |
| 2005/0257335 A1 | 11/2005 | Dumousseaux | |
| 2005/0257715 A1 | 11/2005 | Dumousseaux | |
| 2005/0260146 A1 | 11/2005 | Blin | |
| 2006/0018854 A1 | 1/2006 | Dumousseaux et al. | |
| 2006/0034875 A1 | 2/2006 | Nakanishi et al. | |
| 2006/0039876 A1 | 2/2006 | Dumousseaux et al. | |
| 2006/0041054 A1 | 2/2006 | Dumousseaux et al. | |
| 2006/0099160 A1 | 5/2006 | Dumousseaux | |
| 2007/0098655 A1 | 5/2007 | Schmaus et al. | |
| 2007/0104662 A1 | 5/2007 | Satonaka et al. | |
| 2007/0134181 A1 | 6/2007 | Shimizu et al. | |
| 2007/0155886 A1 * | 7/2007 | Sheerin | C09D 5/028 524/432 |
| 2008/0044366 A1 | 2/2008 | Dumousseaux | |
| 2008/0051472 A1 | 2/2008 | Kwetkat et al. | |
| 2009/0185991 A1 | 7/2009 | Spaulding et al. | |
| 2009/0186055 A1 | 7/2009 | Dumousseaux et al. | |
| 2009/0324654 A1 * | 12/2009 | Polonka et al. | 424/401 |
| 2010/0003204 A1 | 1/2010 | Loy et al. | |
| 2010/0055028 A1 | 3/2010 | Scott et al. | |
| 2010/0098765 A1 | 4/2010 | Mercado et al. | |
| 2010/0272663 A1 * | 10/2010 | Pierre et al. | 424/64 |
| 2012/0015016 A1 | 1/2012 | Galdi et al. | |
| 2012/0082708 A1 | 4/2012 | Lee et al. | |
| 2013/0309285 A1 | 11/2013 | Matsufuji et al. | |
| 2015/0190320 A1 | 7/2015 | Tachon et al. | |
| 2015/0290090 A1 | 10/2015 | Matsufuji et al. | |
| 2015/0290109 A1 | 10/2015 | Simonnet et al. | |

FOREIGN PATENT DOCUMENTS

| | | |
|---|---|---|
| DE | 676103 C | 5/1939 |
| DE | 4227391 C1 | 9/1993 |
| DE | 19608117 A1 | 9/1997 |
| DE | 19622612 C1 | 10/1997 |
| DE | 19631225 A1 | 2/1998 |
| DE | 19647060 A1 | 5/1998 |
| DE | 19726184 A1 | 12/1998 |
| DE | 19750245 A1 | 5/1999 |
| DE | 19750246 A1 | 5/1999 |
| DE | 19855649 A1 | 6/2000 |
| DE | 19943668 A1 | 3/2001 |
| DE | 19943681 A1 | 3/2001 |
| DE | 10027950 A1 | 12/2001 |
| DE | 10138499 A1 | 2/2003 |
| EP | 0242219 A2 | 10/1987 |
| EP | 0285886 A1 | 10/1988 |
| EP | 0293795 A1 | 12/1988 |
| EP | 0295886 A2 | 12/1988 |
| EP | 0390683 A1 | 10/1990 |
| EP | 0425324 A1 | 5/1991 |
| EP | 0524109 A1 | 1/1993 |
| EP | 0425324 B1 | 10/1993 |
| EP | 0576974 A1 | 1/1994 |
| EP | 0669323 A1 | 8/1995 |
| EP | 0693471 A1 | 1/1996 |
| EP | 0694521 A1 | 1/1996 |
| EP | 0697244 A1 | 2/1996 |
| EP | 0697245 A1 | 2/1996 |
| EP | 0708079 A1 | 4/1996 |
| EP | 0712855 A1 | 5/1996 |
| EP | 0714880 A1 | 6/1996 |
| EP | 0743309 A1 | 11/1996 |
| EP | 0761201 A1 | 3/1997 |
| EP | 0765656 A1 | 4/1997 |
| EP | 0790243 A1 | 8/1997 |
| EP | 0893119 A1 | 1/1999 |
| EP | 0895779 A1 | 2/1999 |
| EP | 0903342 A1 | 3/1999 |
| EP | 0921126 A1 | 6/1999 |
| EP | 1055642 A2 | 11/2000 |
| EP | 1069142 A1 | 1/2001 |
| EP | 1092421 A2 | 4/2001 |
| EP | 1270686 A2 | 1/2003 |

(56) References Cited

FOREIGN PATENT DOCUMENTS

| | | |
|---|---|---|
| FR | 2315991 A1 | 1/1977 |
| FR | 2395023 A1 | 1/1979 |
| FR | 2416008 A1 | 8/1979 |
| FR | 2466492 A1 | 4/1981 |
| FR | 2506156 A1 | 11/1982 |
| FR | 2528420 A1 | 12/1983 |
| FR | 2529887 A1 | 1/1984 |
| FR | 2638354 A1 | 5/1990 |
| FR | 2639347 A1 | 5/1990 |
| FR | 2651126 B1 | 12/1991 |
| FR | 2840806 A1 | 12/2003 |
| FR | 2868694 A1 | 10/2005 |
| FR | 2886853 A1 | 12/2006 |
| GB | 1539625 A | 1/1979 |
| GB | 2286774 A | 8/1995 |
| GB | 2303549 A | 2/1997 |
| GB | 2319523 A | 5/1998 |
| JP | 61-194013 A | 8/1986 |
| JP | S61194009 A | 8/1986 |
| JP | H01158090 A | 6/1989 |
| JP | H01-190625 A | 7/1989 |
| JP | H02295912 A | 12/1990 |
| JP | H03-181584 A | 8/1991 |
| JP | H03-200721 A | 9/1991 |
| JP | H03-243666 A | 10/1991 |
| JP | H04134041 A | 5/1992 |
| JP | H04134042 A | 5/1992 |
| JP | H04134043 A | 5/1992 |
| JP | H04-198124 A | 7/1992 |
| JP | H04-230305 A | 8/1992 |
| JP | H04290882 A | 10/1992 |
| JP | H05-238924 A | 9/1993 |
| JP | H07-149914 A | 6/1995 |
| JP | 08-311003 A | 11/1996 |
| JP | 2628058 B | 7/1997 |
| JP | H09-286928 A | 11/1997 |
| JP | 09-309815 A | 12/1997 |
| JP | 10-017593 A | 1/1998 |
| JP | 10212421 A | 8/1998 |
| JP | H10-338612 A | 12/1998 |
| JP | H10-338616 A | 12/1998 |
| JP | H11-21468 A | 1/1999 |
| JP | 11-060437 A | 3/1999 |
| JP | H11-255630 A | 9/1999 |
| JP | H11-302625 A | 11/1999 |
| JP | 2000-080021 A | 3/2000 |
| JP | 2000-247824 A | 9/2000 |
| JP | 2001-072527 A | 3/2001 |
| JP | 2001-098186 A | 4/2001 |
| JP | 2001-199857 A | 7/2001 |
| JP | 2001-323070 A | 11/2001 |
| JP | 2002-338428 A | 11/2002 |
| JP | 2002-363435 A | 12/2002 |
| JP | 2003-012504 A | 1/2003 |
| JP | 2003-160744 A | 6/2003 |
| JP | 2004-231952 A | 8/2004 |
| JP | 2006-040546 A | 2/2006 |
| JP | 2007-126419 A | 5/2007 |
| JP | 2007-277057 A | 10/2007 |
| JP | 2007254429 * | 10/2007 |
| JP | 2007254429 | 10/2007 |
| JP | 2008-031138 A | 2/2008 |
| JP | 2009-091203 A | 4/2009 |
| JP | 2010-120871 A | 6/2010 |
| JP | 2011-512376 A | 4/2011 |
| JP | 2011-118046 A | 6/2011 |
| JP | 2011-236193 A | 11/2011 |
| WO | 92/06778 A1 | 4/1992 |
| WO | 9304665 A1 | 3/1993 |
| WO | 9310753 A1 | 6/1993 |
| WO | 9311095 A1 | 6/1993 |
| WO | 9505150 A1 | 2/1995 |
| WO | 96/16930 A1 | 6/1995 |
| WO | 9522959 A2 | 8/1995 |
| WO | 96/14926 A1 | 5/1996 |
| WO | 96/16930 A1 | 6/1996 |
| WO | 96/25384 A1 | 8/1996 |
| WO | 96/25388 A1 | 8/1996 |
| WO | 9703642 A1 | 2/1997 |
| WO | 97/25970 A1 | 7/1997 |
| WO | 97/31890 A1 | 9/1997 |
| WO | 96/40124 A1 | 10/1997 |
| WO | 97/35842 A1 | 10/1997 |
| WO | 9822447 A1 | 5/1998 |
| WO | 9825922 A1 | 6/1998 |
| WO | 99/10318 A1 | 3/1999 |
| WO | 99/22707 A1 | 5/1999 |
| WO | 99/32077 A1 | 7/1999 |
| WO | 02/26211 A1 | 4/2002 |
| WO | 03/024412 A2 | 3/2003 |
| WO | 2004/024798 A1 | 3/2004 |
| WO | 2004/085412 A2 | 10/2004 |
| WO | 2004/105736 A1 | 12/2004 |
| WO | 2006/034982 A1 | 4/2006 |
| WO | 2006/034985 A1 | 4/2006 |
| WO | 2006/034991 A1 | 4/2006 |
| WO | 2006/034992 A1 | 4/2006 |
| WO | 2006/035000 A1 | 4/2006 |
| WO | 2006/035007 A1 | 4/2006 |
| WO | 2009/103602 A1 | 8/2009 |
| WO | 2010/078985 A2 | 7/2010 |
| WO | 2010/098249 A1 | 9/2010 |
| WO | 2011/016139 A1 | 2/2011 |
| WO | 2011/016143 A1 | 2/2011 |
| WO | 2011016144 | 2/2011 |
| WO | 2011/150034 A2 | 12/2011 |
| WO | 2011/151184 A1 | 12/2011 |
| WO | 2012/069291 A1 | 5/2012 |
| WO | 2014010098 A1 | 1/2014 |
| WO | 2014010101 A1 | 1/2014 |

OTHER PUBLICATIONS

Gera, Manoj et al., "Mechanical Methods for Dry Particle Coating Processes and Their Applications in Drug Delivery and Development," Recent Patents on Drug Delivery & Formulation, XP55059149, vol. 4, No. 1, Jan. 1, 2010, pp. 58-81.
Bacsa et al., "CVD Synthesis of Shape and Size Controlled ZnO Nanoparticles for Application as UV Filters," ECS Transactions, The Electrochemical Society, XP009149325, vol. 25, No. 8, Jan. 1, 2009, pp. 1177-1183.
Todd, Charles, et al., "Volatile Silicone Fluids for Cosmetic Formulations," Cosmetics and Toiletries, vol. 91, 1976, pp. 27-32.
Contado et al., "TiO2 in Commercial Sunscreen Lotion: Flow Field-Flow Fractionation and ICP-AES Together for Size Analysis," Anal. Chem., XP-002642392, vol. 80, 2008, pp. 7594-7608.
English Language Abstract for FR2886853 (Dec. 15, 2006).
International Search Report and Written Opinion for PCT/JP2012/068524. (dated Aug. 5, 2013).
International Search Report for PCT/JP2012/068532 (dated May 3, 2013).
English language abstract for DE 19726184 (Dec. 24, 1998).
English language abstract for DE 676103 (May 25, 1939).
English language abstract for EP 0285886 (Oct. 12, 1988).
English language abstract for EP 0390683 (Oct. 3, 1990).
English language abstract for FR 2395023 (Jan. 19, 1979).
English language abstract for JP H01-158090 (Jun. 21, 1989).
English language abstract for JP H02-295912 (Dec. 6, 1990).
English language abstract for JP H04-134041 (May 7, 1992).
English language abstract for JP H04-134042 (May 7, 1992).
English language abstract for JP H04-134043 (May 7, 1992).
English language abstract for JP H04-290882 (Oct. 15, 1992).
English language abstract for JP S61-194009 (Aug. 28, 1986).
Japanese Office Action for JP 2015-521147, dated Mar. 7, 2016.
Japanese Office Action for JP 2015-521149, dated Mar. 7, 2016.
Chinese Office Action for CN 201280074100.8, dated Mar. 31, 2016.
English language Abstract for EP 0425324 B1 (Oct. 27, 1993).
International Search Report and Written Opinion for PCT/JP2012/053032 (dated Apr. 24, 2012).

(56) References Cited

OTHER PUBLICATIONS

International Search Report for PCT/JP2011/052965 (dated Jun. 30, 2011).
Japanese Office Action for copending Japanese Application 2013/0535177 (dated Nov. 2, 2015) (with translation).
Restriction Requirement for copending U.S. Appl. No. 13/983,183 (dated Feb. 6, 2015).
Non-Final Office Action for copending U.S. Appl. No. 13/983,183 (dated Jun. 1, 2015).
Final Office Action for copending U.S. Appl. No. 13/983,183 (dated Oct. 15, 2015).
Non-Final Office Action for copending U.S. Appl. No. 13/983,183 (dated Feb. 11, 2016).
Shin-Etsu Technical Data Sheet, KSG-15 (Sep. 12, 2012).
Shin-Etsu Technical Data Sheet, KSG-16 (Sep. 12, 2012).
Shin-Etsu Technical Data Sheet, KSG-18A (May 9, 2013).
Japanese Office Action for copending Japanese Application 2015/521150 (dated Feb. 22, 2016) (with translation).
European Patent Office Action for copending European Application 12709183 (dated Feb. 24, 2016).
Tsugio, Sato et al., "Synthesis and UV-shielding Properties of Calcia-Doped Ceria Nanoparticles Coated with Amorphous Silica," Solid State Ionics, 172, (2004), pp. 377-382.
Restriction Requirement for copending U.S. Appl. No. 14/413,505 (dated Sep. 10, 2015).
Non-Final Office Action for copending U.S. Appl. No. 14/413,505 (dated Feb. 22, 2016).
Restriction Requirement for copending U.S. Appl. No. 14/412,777 (dated Dec. 21, 2015).
Non-Final Office Action for copending U.S. Appl. No. 14/412,777 (dated Mar. 10, 2016).
English language Abstract for DE 19622612C1 (Oct. 23, 1997).
English language Abstract for DE 19631225 A1 (Feb. 5, 1998).
English language Abstract for DE 19647060 A1 (May 20, 1998).
English language Abstract for DE 19750245 A1 (May 20, 1999).
English language Abstract for DE 19750246 A1 (May 20, 1999).
English language Abstract for DE 19943681 A1 (Mar. 15, 2001).
English language Abstract for EP 0425324 A1 (May 2, 1991).
English language Abstract for FR 2651126 B1 (Dec. 6, 1991).
English language Abstract for FR 2840806 A1 (Dec. 19, 2003).
English language Abstract for JPH01-190625A (Jul. 31, 1989).
English language Abstract for JPH03-181584A (Aug. 7, 1991).
English language Abstract for JPH03-200721A (Sep. 2, 1991).
English language Abstract for JPH03-243666A (Oct. 30, 1991).
English language Abstract for JP05-238924A (Sep. 17, 1993).
English language Abstract for JPH07-149914A (Jun. 13, 1995).
English language machine translation of JP8-311003A (Nov. 26, 1996).
English language Abstract for JPH09-286928A (Nov. 4, 1997).
English language machine translation of JP10-017593A (Jan. 20, 1998).
English language Abstract for JP10-338612A (Dec. 22, 1998).
English language Abstract for JP10-338616A (Dec. 22, 1998).
English language machine translation of JP11-060437A (Mar. 2, 1999).
English language Abstract for JPH11-255630A (Sep. 21, 1999).
English language Abstract for JP2000-080021A (Mar. 21, 2000).
English language Abstract for JP2003-012504A (Jan. 15, 2003).
English language Abstract for JP2004-231952A (Aug. 19, 2004).
English language Abstract for JP2006-040546A (Feb. 9, 2006).
English language Abstract for JP2009-091203A (Apr. 30, 2009).
English language Abstract for JP2010-120871A (Jun. 3, 2010).
English language Abstract for JP2011-118046A (Jun. 16, 2011).
English language Abstract for JP2011-236193A (Nov. 24, 2011).
Notice of Allowance for counterpart JP Application No. 2015-521150, dated Jan. 30, 2017.
European Office Action received in connection with European Application No. EP12745921.2; dated Jul. 4, 2017.
Office Action for counterpart Application JP2013-535177, dated Oct. 2, 2017.
Office Action for counterpart U.S. Appl. No. 14/412,777, dated Apr. 10, 2018.
TSD BN Product Cosmetics (http://www.topspindesign.com/business/bn_cosmetic.htm 2010).
Point of Interest! (Mineral-make up ingredients: Boron nitride: http://swiftcraftymonkey.blogspot.com/2009/08/mineral-make-up-ingredients-boron.html) Aug. 16, 2009.
Advisory Action Issued in related U.S. Appl. No. 14/412,777 dated Jan. 19, 2018.
Non-Final Office Action for copending U.S. Appl. No. 15/404,563, dated Dec. 4, 2018.
Final Office Action for co-pending U.S. Appl. No. 14/413,505, dated Apr. 17, 2019.
Non-Final Office Action for co-pending U.S. Appl. No. 15/404,563, dated Sep. 20, 2019.
Liang, H. et al., "UV Protection Effectiveness of Plastic Particles Coated with Titanium Dioxide by Rotational Impact Blending," Institution of Chemical Engineers, Trans IChemE, vol. 78, Part A, Jan. 2000, pp. 49-54.
Final Office Action for copending U.S. Appl. No. 15/404,563, dated Feb. 13, 2020.
Jaroenworaluck, A. et al., "Characteristics of Silica-Coated TiO2 and its UV Absorption for SunScreen Cosmetic Applications," Surface and Interface Analysis, vol. 38, Issue 4, Mar. 29, 2006, pp. 473-477.
Non-Final Office Action for copending U.S. Appl. No. 14/413,505, dated Dec. 17, 2020.
English Abstract for "Sunscreen: According to the current state of knowledge zinc oxide as UV filter is safe," BfR Opinion No. 037/2010, Jun. 18, 2010, Internet, URL, "http://www.bfr.bund.de.cm/206/sonnenschultzmittel_zinkoxid_als_uv_filter_ist_nach_derzeitigern_kenntnisstand_gesundheitlich_unbendlich.pdf".
Partial Machine Translation of Opposition to EP 2 872 106 B1, dated May 10, 2021.

* cited by examiner

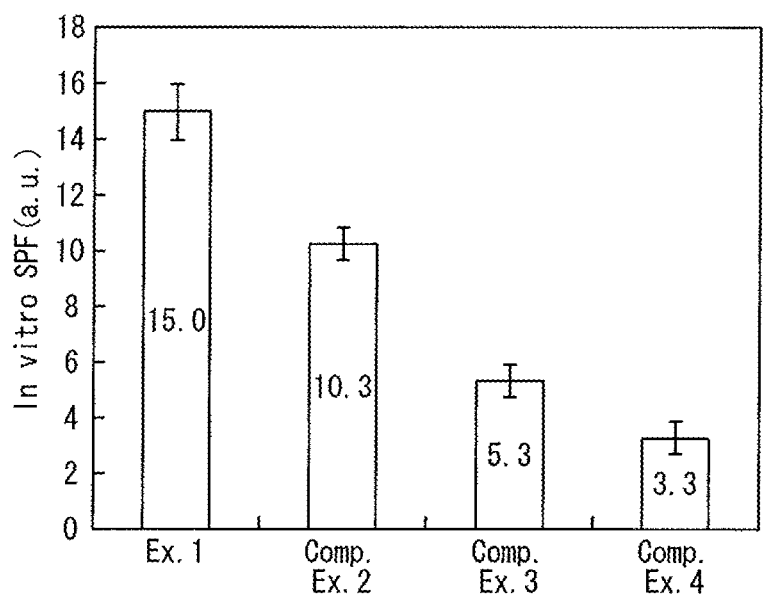

COSMETIC COMPOSITION COMPRISING COMPOSITE SUNSCREEN PARTICLES

CROSS REFERENCE TO RELATED APPLICATIONS

This is a national stage application of PCT/JP2012/068526, filed internationally on Jul. 13, 2012.

TECHNICAL FIELD

The present invention relates to a cosmetic composition comprising a combination of at least one specific composite pigment, at least one organopolysiloxane elastomer, and at least one specific oil absorbing agent in a specific amount condition.

BACKGROUND ART

Imperfections of the skin are visible, because of the contrast between bright areas such as skin ridges and dark areas such as skin pores. Light scattering can decrease this brightness gap, and may be achieved by mat and haze effects. A good balance between the oil absorption capacity of filler(s) and the amount of non-volatile oil(s) in a cosmetic composition to be applied onto the skin for hiding skin pores may provide a mat effect. Introduction of filler(s) with light scattering properties into the cosmetic composition may provide a haze effect.

Sebum secretion during the day tends in particular to alter optical effects achieved just after the application of a cosmetic composition on the skin for hiding skin pores. In order to increase the length of time of the initial pore hiding effect, filler(s) with a large oil absorption capacity may be introduced in the cosmetic composition to absorb an excess amount of sebum.

On another aspect, UV protection can be achieved by the introduction of organic or inorganic UV filter(s) into a cosmetic composition. Organic UV filters may provide strong UVA and UVB protection but bring inappropriate level of shine to the cosmetic composition. Inorganic UV filters such as $TiO_2$ and ZnO pigments have good light scattering properties but inappropriate sensory profile.

US-A-2005/163730 discloses a combination of a ZnO nanopigment, a silicone elastomer and a plate-type filler such as $TiO_2$-coated mica or bismuth oxychloride.

However, there is still a need to provide a cosmetic composition having pore hiding effect with long lasting and improved UV filtering effects.

DISCLOSURE OF INVENTION

An objective of the present invention is to provide a cosmetic composition with improved skin pore hiding effects and improved UV filtering effects, which can last for a long period of time, without deteriorating other cosmetic effects such as skin brightening, color homogeneity and smoothening effects.

The above objective can be achieved by a cosmetic composition comprising:
(i) at least one composite pigment comprising at least one small particle with a mean particle size of more than 100 nm and less than 1 µm, preferably less than 600 nm, and more preferably less than 400 nm, wherein the surface of the small particle is at least in part covered with at least one coating layer comprising at least one inorganic or organic particulate solid UV filter and optionally at least one coloring pigment, preferably at least one coating layer comprising at least one inorganic or organic particulate solid UV filter, and more preferably at least one inorganic solid UV filter;
(ii) at least one organopolysiloxane elastomer, preferably non-emulsifying organopolysiloxane elastomer; and
(iii) at least one oil absorbing agent with oil absorption capability of 1 ml/1 g or more in an amount of more than 1% by weight relative to the total weight of composition.

The small particle may be preferably a small hollow particle.

The composite pigment may further comprise at least one large particle with a mean particle size of 2 µm or more, preferably 3 µm or more, more preferably 4 µm or more, and even more preferably 5 µm or more, wherein the surface of the large particle is optionally at least in part covered with at least one coating layer comprising at least one inorganic or organic particulate solid UV filter and/or at least one coloring pigment.

The coating layer on the small and/or large particle(s) may have a thickness of from 1 nm to 50 nm, preferably from 5 nm to 40 nm, and more preferably from 10 nm to 30 nm.

The inorganic solid UV filter may be selected from the group consisting of silicon carbide, metal oxides, and mixtures thereof. It is preferable that the inorganic solid UV filter be titanium dioxide.

The inorganic solid UV filter may have a mean particle size of from 1 nm to 50 nm, preferably from 5 nm to 40 nm, and more preferably from 10 nm to 30 nm.

The small particle or the large particle may comprise at least one inorganic material and/or at least one organic material, preferably at least one organic material advantageously selected from the group consisting of poly(meth)acrylates, polyamides, silicones, polyurethanes, polyethylenes, polypropylenes, polystyrenes, copolystyrenes, polyhydroxyalkanoates, polycaprolactams, poly(butylene) succinates, polysaccharides, polypeptides, polyvinyl alcohols, polyvinyl resins, fluoropolymers, wax, amidosulfonic acid polyvalent metal salts, acylated amino acids, and mixtures thereof.

As the organic material, the small particle may preferably contain at least one organic polymer. In particular, as the organic polymer, copolystyrene is preferable, and styrene/acrylate copolymer, and cross-linked styrene/methyl methacrylate copolymer are more preferable.

The small particle may comprise at least one copolystyrene, preferably a styrene/acrylate copolymer, and/or a cross-linked styrene/methyl methacrylate copolymer;
the large particle may comprise at least one poly(meth)acrylate, preferably a methyl methacrylate polymer; and
the small and large particles may be at least in part covered with at least one coating layer comprising metal oxide, preferably titanium oxide.

The composite pigment based on a small particle can be obtained by subjecting:
at least one small particle with a mean particle size more than 100 nm and of less than 1 µm, preferably less than 600 nm, and more preferably less than 400 nm;
at least one inorganic or organic particulate solid UV filter; and
optionally at least one coloring pigment and/or at least one additional UV filter to a mechanochemical fusion process.

The composite pigment based on small and large particles can be obtained by subjecting:
at least one small particle with a mean particle size more than 100 nm and of less than 1 µm, preferably less than 600 nm, and more preferably less than 400 nm;

at least one large particle with a mean particle size of 2 µm or more, preferably 3 µm or more, more preferably 4 µm or more, and even more preferably 5 µm or more;

at least one inorganic or organic particulate solid UV filter; and optionally at least one coloring pigment and/or at least one additional UV filter to a mechanochemical fusion process.

The organopolysiloxane elastomer may be non-emulsifying organopolysiloxane elastomer in form of a gel or powder.

The organopolysiloxane elastomer may be present in an amount ranging from 0.1% to 20% by weight, preferably ranging from 0.5% to 15% by weight, and more preferably ranging from 0.5% to 10% by weight relative to the total weight of the composition.

The oil absorbing agent may be present in the composition in an amount ranging from 1% to 40% by weight of the composition, and preferably from 2% to 20% by weight relative to the total weight of the composition.

The oil absorbing agent may be chosen from silicas, polyamide (in particular Nylon-6) powders, powders of acrylic polymers, especially of polymethyl methacrylate, of polymethyl methacrylate/ethylene glycol dimethacrylate, of polyallyl methacrylate/ethylene glycol dimethacrylate or of ethylene glycol dimethacrylate/lauryl methacrylate copolymer; perlites; magnesium carbonate, and mixtures thereof.

It is preferable that the oil absorbing agent be chosen from powders of acrylic polymers, especially of polymethyl methacrylate.

The cosmetic composition according to the present invention may be in the form of a liquid, powder or aerosol foam.

In a particular embodiment, the cosmetic composition of the present invention is a base or a primer, in particular a skin care or a make-up base or primer.

In a particular embodiment, the cosmetic composition of the present invention may comprise a low amount of additional coloring pigments as coloring pigments in high amount may tend to accumulate inside the pores and enhance their visibility.

The term 'additional coloring pigments' according to the present invention means here additional coloring pigments used as ingredients dispersed in the cosmetic composition according to the present invention, which are distinct from the coloring pigments that may be present in the coating of the said composite pigments.

Then, the cosmetic composition according to the present invention may comprise from 0 to 5% of additional coloring pigments relative to the total weight of the composition.

In a particular embodiment, the cosmetic composition according to the present invention comprises from 0 to 3% of additional coloring pigments relative to the total weight of the composition.

Another objective of the present invention is to provide a cosmetic process with advantageous cosmetic and/or practical effects by using the cosmetic composition according to the present invention.

The above objective can be achieved by applying the cosmetic composition according to the present invention onto the skin.

Thus, the present invention also relates to a cosmetic process for improving UV filtration and/or pore hiding on the skin, with long lasting, comprising the application on the skin of at least one layer of the cosmetic composition according to the present invention.

BRIEF DESCRIPTION OF DRAWINGS

FIG. 1 shows a graph showing the in vitro SPF values of the cosmetic compositions according to Example 1 and Comparative Examples 2 to 4.

BEST MODE FOR CARRYING OUT THE INVENTION

After diligent research, the inventors have discovered that it is possible to provide a cosmetic composition with both improved skin pore hiding effects and improved UV filtering effects, which can last for a long period of time, without deteriorating cosmetic effects such as skin brightening, color homogeneity and smoothening effects, by combining three specific elements.

Thus, the cosmetic composition according to the present invention comprises, at least:

(i) at least one composite pigment comprising at least one small particle with a mean particle size of more than 100 nm and less than 1 µm, preferably less than 600 nm, and more preferably less than 400 nm, wherein the surface of the small particle is at least in part covered with at least one coating layer comprising at least one inorganic or organic particulate solid UV filter, and optionally at least one coloring pigment, preferably at least one coating layer comprising at least one inorganic or organic particulate solid UV filter, and more preferably at least one inorganic solid UV filter;

(ii) at least one organopolysiloxane elastomer; and (iii) at least one oil absorbing agent with oil absorption capability of 1 ml/1 g or more in an amount of more than 1% by weight relative to the total weight of composition.

It is preferable that the composite pigment further comprise at least one large particle with a mean particle size of 2 µm or more, preferably 3 µm or more, more preferably 4 µm or more, and even more preferably 5 µm or more, wherein the surface of the large particle is optionally at least in part covered with at least one coating layer comprising at least one inorganic or organic particulate solid UV filter and/or at least one coloring pigment.

This cosmetic composition according to the present invention can decrease the visibility of skin pores once applied on the skin (the skin pore hiding effects can last for a long time such as all day long), while providing enhanced UV protection, without deteriorating other cosmetic properties such as bright skin look, homogeneous skin color, and smooth feeling to touch.

Hereafter, each of the elements constituting the cosmetic composition according to the present invention will be described in a detailed manner.

[Composite Pigment]

The cosmetic composition according to the present invention includes at least one specific composite pigment comprising, at least one small particle wherein the surface of the small particle is at least in part covered with at least one coating layer comprising at least one inorganic or organic particulate solid UV filter.

(Small Core Particle)

The small core particle for the composite pigment used in the present invention is not limited, as long as the small core particle has a mean particle size or a mean particle diameter of more than 100 nm and less than 1 µm, preferably less than 600 nm, and more preferably less than 400 nm. The small core particle may be in the form of a solid or hollow particle, preferably a hollow particle.

The mean particle size or mean particle diameter here is an arithmetic mean diameter, and can be determined, for example, by calculating the average of the dimensions of one hundred particles chosen on an image obtained with a scanning electron microscope.

The small core particle can be in any shape. For example, it is possible to use a small core particle in the form of a plate with an aspect ratio of at least 5, preferably more than 10, more preferably more than 20, and more preferably more than 50. The aspect ratio can be determined by the average thickness and the average length according to the formula: aspect ratio=length/thickness.

If a plate-like particle is used for the present invention, it is preferable that the plate-like particle have a length ranging from more than 100 nm to less than 1 μm, preferably less than 600 nm, and more preferably less than 400 nm.

In a preferred embodiment, the small core particle has a spherical shape.

The material of the small core particle is not limited. The material can be at least one inorganic material and/or at least one organic material, preferably at least one organic material.

The inorganic material and/or organic material may be porous. The porosity of the material may be characterized by a specific surface area of from $0.05\ m^2/g$ to $1,500\ m^2/g$, more preferably from $0.1\ m^2/g$ to $1,000\ m^2/g$, and more preferably from $0.2\ m^2/g$ to $500\ m^2/g$ according to the BET method.

Preferably, the inorganic material can be selected from the group consisting of mica, synthetic mica, talc, sericite, boron nitride, glass flakes, calcium carbonate, barium sulfate, titanium oxide, hydroxyapatite, silica, silicate, zinc oxide, magnesium sulfate, magnesium carbonate, magnesium trisilicate, aluminum oxide, aluminum silicate, calcium silicate, calcium phosphate, magnesium oxide, bismuth oxychloride, kaolin, hydrotalcite, mineral clay, synthetic clay, iron oxide, and mixtures thereof. In particular, natural mica, synthetic mica, sericite, kaolin, talc and mixtures thereof are preferable.

Preferably, the organic material can be selected from the group consisting of poly(meth)acrylates, polyamides, silicones, polyurethanes, polyethylenes, polypropylenes, polystyrenes, copolystyrenes, polyhydroxyalkanoates, polycaprolactams, poly(butylene) succinates, polysaccharides, polypeptides, polyvinyl alcohols, polyvinyl resins, fluoropolymers, waxes, amidosulfonic acid polyvalent metal salts, acylated amino acids, and mixtures thereof. As fluoropolymers, for example, PTFE may be used. As amidosulfonic acid polyvalent metal salts, for example, N-lauroyltaurine calcium may be used. As acylated amino acids, lauroyllysine may be used. Polyamides such as Nylon®, polyhydroxyalkanoates such as polylactic acids, poly(meth)acrylates such as polymethylmethacrylates, silicones, and mixtures thereof are more preferable.

In particular, as the organic material, copolystyrene is preferable, and styrene/acrylate copolymer, and cross-linked styrene/methyl methacrylate copolymer are more preferable. Thus, as the small core particles, for example, Sunspheres (small hollow particles made from styrene/acrylate copolymer) marketed by Rohm and Haas, as well as SX859(A) and SX866(B) (small hollow particles made from cross-linked styrene/methyl methacrylate copolymer) marketed by JSR Corp. in Japan, are preferable. In addition, polymethylmethacrylate solid small particles such as MP2200 marketed by Soken in Japan are also preferable as organic small core particles.

The small core particle may or may not be coated beforehand.

In a particular embodiment, the small core particle is originally coated. The material of an original coating of the small core particle is not limited, but an organic material such as an amino acid, an N-acylamino acid, an amido, a silicone and a modified silicone, may be preferable. As the organic material, mention may be made of lauroyl lysine and acryl-modified silicone.

(Layer on Small Core Particle)

The small core particle is at least partially covered with at least one layer comprising at least one inorganic or organic particulate solid UV filter, preferably at least one inorganic solid UV filter. The layer may be referred to as a coating layer. Preferably, 10% or more of the surface of the small core particle can be covered by the coating layer(s). More preferably, 50% or more of the surface of the small core particle can be covered by the coating layer(s). More preferably, 80% or more of the small core particle can be covered by the coating layer(s). Most preferably, the entire surface of the small core particle can be covered by the coating layer(s).

The thickness of the coating layer may vary depending on several factors such as the size of the small core particle. Typically, the thickness of the coating layer may range from 1 nm to 50 nm, preferably from 5 nm to 40 nm, and more preferably from 10 nm to 30 nm.

If there are two or more coating layers on the small core particle, the thickness and the composition of the coating layers may be the same as or different from each other.

The coating layer(s) may comprise, other than the inorganic or organic particulate solid UV filter(s), any additional material(s) such as coloring pigment(s) and/or additional UV filter(s), preferably liquid UV filter(s). The additional material(s) may be present in an amount ranging from 1 to 50 wt % relative to the total weight of the additional material(s) and the inorganic or organic particulate solid UV filter(s).

(Inorganic Solid UV Filter)

As described above, the coating layer(s) on the small core particle may comprise at least one inorganic solid UV filter. If two or more inorganic solid UV filters are used, they may be the same or different, preferably the same.

The inorganic solid UV filter used for the present invention may be active in the UV-A and/or UV-B region, preferably in the UV-B region or in the UV-A and UV-B region. It is preferable that the active UV filtering region of the inorganic solid UV filter and that of the particulate organic solid UV filter be complementary to each other, in order to provide comprehensive UV protection. For example, it is preferable that the inorganic solid UV filter be active at least in the UV-B region and the particulate organic solid UV filter be active at least in the UV-A region. The inorganic solid UV filter may be hydrophilic and/or lipophilic. The inorganic solid UV filter is completely insoluble in solvents such as water and ethanol commonly used in cosmetics. The term "solid" means solid at 25° C. under 1 atm.

It is preferable that the inorganic solid UV filter be in the form of a fine particle such that the mean (primary) particle diameter thereof ranges from 1 nm to 50 nm, preferably from 5 nm to 40 nm, and more preferably from 10 nm to 30 nm. The mean (primary) particle size or mean (primary) particle diameter here is an arithmetic mean diameter.

The inorganic solid UV filter may be selected from the group consisting of silicon carbide, metal oxides which may or may not be coated, and mixtures thereof.

Preferably, the inorganic solid UV filters are selected from pigments (mean size of the primary particles: generally from 5 nm to 50 nm, preferably from 10 nm to 50 nm) formed of metal oxides, such as, for example, pigments formed of titanium oxide (amorphous or crystalline in the rutile and/or anatase form), iron oxide, zinc oxide, zirconium oxide or cerium oxide, which are all UV photoprotective agents well known per se. Preferably, the inorganic solid UV filters are selected from titanium oxide, zinc oxide, and more preferably titanium oxide.

The inorganic solid UV filter may or may not be coated. The inorganic solid UV filter may have at least one coating. The coating may comprise at least one compound selected from the group consisting of alumina, silica, aluminum hydroxide, silicones, silanes, fatty acids or salts thereof (such as sodium, potassium, zinc, iron or aluminum salts), fatty alcohols, lecithin, amino acids, polysaccharides, proteins, alkanolamines, waxes such as beeswax, (meth)acrylic polymers, organic UV filters, and (per)fluoro compounds.

It is preferable for the coating to include at least one organic UV filter. As the organic UV filter in the coating, a dibenzoylmethane derivative such as butyl methoxydibenzoylmethane (Avobenzone) and 2,2'-Methylenebis[6-(2H-Benzotriazol-2-yl)-4-(1,1,3,3-Tetramethyl-Butyl)Phenol] (Methylene Bis-Benzotriazolyl Tetramethylbutylphenol) marketed as "TINOSORB M" by BASF may be preferable.

In a known manner, the silicones in the coating(s) may be organosilicon polymers or oligomers comprising a linear or cyclic and branched or cross-linked structure, of variable molecular weight, obtained by polymerization and/or polycondensation of suitable functional silanes and essentially composed of a repetition of main units in which the silicon atoms are connected to one another via oxygen atoms (siloxane bond), optionally substituted hydrocarbon radicals being connected directly to the said silicon atoms via a carbon atom.

The term "silicones" also encompasses silanes necessary for their preparation, in particular alkylsilanes.

The silicones used for the coating(s) can preferably be selected from the group consisting of alkylsilanes, polydialkylsiloxanes and polyalkylhydrosiloxanes. More preferably still, the silicones are selected from the group consisting of octyltrimethylsilane, polydimethylsiloxanes and polymethylhydrosiloxanes.

Of course, the inorganic solid UV filters made of metal oxides may, before their treatment with silicones, have been treated with other surfacing agents, in particular with cerium oxide, alumina, silica, aluminum compounds, silicon compounds or their mixtures.

The coated inorganic solid UV filter may have been prepared by subjecting the inorganic solid UV filter to one or more surface treatments of a chemical, electronic, mechanochemical and/or mechanical nature with any of the compounds as described above, as well as polyethylenes, metal alkoxides (titanium or aluminum alkoxides), metal oxides, sodium hexametaphosphate, and those shown, for example, in Cosmetics & Toiletries, February 1990, Vol. 105, pp. 53-64.

The coated inorganic solid UV filters may be titanium oxides coated:
with silica, such as the product "Sunveil" from Ikeda;
with silica and with iron oxide, such as the product "Sunveil F" from Ikeda;
with silica and with alumina, such as the products "Microtitanium Dioxide MT 500 SA" from Tayca, "Tioveil" from Tioxide, and "Mirasun TiW 60" from Rhodia;
with alumina, such as the products "Tipaque TTO-55 (B)" and "Tipaque TTO-55 (A)" from Ishihara, and "UVT 14/4" from Kemira;
with alumina and with aluminum stearate, such as the product "Microtitanium Dioxide MT 100 T, MT 100 TX, MT 100 Z or MT-01" from Tayca, the products "Solaveil CT-10 W" and "Solaveil CT 100" from Uniqema, and the product "Eusolex T-AVO" from Merck;
with alumina and with aluminum laurate, such as the product "Microtitanium Dioxide MT 100 S" from Tayca;
with iron oxide and with iron stearate, such as the product "Microtitanium Dioxide MT 100 F" from Tayca;
with zinc oxide and with zinc stearate, such as the product "BR351" from Tayca;
with silica and with alumina and treated with a silicone, such as the products "Microtitanium Dioxide MT 600 SAS", "Microtitanium Dioxide MT 500 SAS" and "Microtitanium Dioxide MT 100 SAS" from Tayca;
with silica, with alumina and with aluminum stearate and treated with a silicone, such as the product "STT-30-DS" from Titan Kogyo;
with silica and treated with a silicone, such as the product "UV-Titan X 195" from Kemira;
with alumina and treated with a silicone, such as the products "Tipaque TTO-55 (S)" from Ishihara or "UV Titan M 262" from Kemira;
with triethanolamine, such as the product "STT-65-S" from Titan Kogyo;
with stearic acid, such as the product "Tipaque TTO-55 (C)" from Ishihara; or
with sodium hexametaphosphate, such as the product "Microtitanium Dioxide MT 150 W" from Tayca.

Other titanium oxide pigments treated with a silicone are preferably $TiO_2$ treated with octyltrimethylsilane and for which the mean size of the individual particles is from 25 and 40 nm, such as that marketed under the trademark "T 805" by Degussa Silices, $TiO_2$ treated with a polydimethylsiloxane and for which the mean size of the individual particles is 21 nm, such as that marketed under the trademark "70250 Cardre UF $TiO_2Si_3$" by Cardre, anatase/rutile $TiO_2$ treated with a polydimethylhydrosiloxane and for which the mean size of the individual particles is 25 nm, such as that marketed under the trademark "Microtitanium Dioxide USP Grade Hydrophobic" by Color Techniques.

Preferably, the following coated $TiO_2$ can be used as the coated inorganic UV filter:
Stearic acid (and) Aluminum Hydroxide (and) $TiO_2$, such as the product "MT-100 TV" from Tayca, with a mean primary particle diameter of 15 nm;
Dimethicone (and) Stearic Acid (and) Aluminum Hydroxide (and) $TiO_2$, such as the product "SA-TTO-S4" from Miyoshi Kasei, with a mean primary particle diameter of 15 nm;
Silica (and) $TiO_2$, such as the product "MT-100 WP" from Tayca, with a mean primary particle diameter of 15 nm;
Dimethicone (and) Silica (and) Aluminum Hydroxide (and) $TiO_2$, such as the product "MT-Y02" and "MT-Y-110 M3S" from Tayca, with a mean primary particle diameter of 10 nm;
Dimethicone (and) Aluminum Hydroxide (and) $TiO_2$, such as the product "SA-TTO-S3" from Miyoshi Kasei, with a mean primary particle diameter of 15 nm;
Dimethicone (and) Alumina (and) $TiO_2$, such as the product "UV TITAN M170" from Sachtleben, with a mean primary particle diameter of 15 nm; and
Silica (and) Aluminum Hydroxide (and) Alginic Acid (and) $TiO_2$, such as the product "MT-100 AQ" from Tayca, with a mean primary particle diameter of 15 nm.

In terms of UV filtering ability, $TiO_2$ coated with at least one organic UV filter is more preferable. For example, Avobenzone (and) Stearic Acid (and) Aluminum Hydroxide (and) TiO$_2$, such as the product "HXMT-100ZA" from Tayca, with a mean primary particle diameter of 15 nm, can be used.

The uncoated titanium oxide pigments are, for example, marketed by Tayca under the trademarks "Microtitanium Dioxide MT500B" or "Microtitanium Dioxide MT600B", by Degussa under the trademark "P 25", by Wacker under the trademark "Oxyde de titane transparent PW", by Miyoshi Kasei under the trademark "UFTR", by Tomen under the trademark "ITS" and by Tioxide under the trademark "Tioveil AQ".

The uncoated zinc oxide pigments are, for example:
those marketed under the trademark "Z-cote" by Sunsmart;
those marketed under the trademark "Nanox" by Elementis; and
those marketed under the trademark "Nanogard WCD 2025" by Nanophase Technologies.

The coated zinc oxide pigments are, for example:
those marketed under the trademark "Oxide Zinc CS-5" by Toshiba (ZnO coated with polymethylhydrosiloxane);
those marketed under the trademark "Nanogard Zinc Oxide FN" by Nanophase Technologies (as a 40% dispersion in Finsolv TN, $C_{12}$-$C_{15}$ alkyl benzoate);
those marketed under the trademark "Daitopersion Zn-30" and "Daitopersion Zn-50" by Daito (dispersions in oxyethylenated polydimethylsiloxane/cyclopolymethylsiloxane comprising 30% or 50% of zinc nano-oxides coated with silica and polymethylhydrosiloxane);
those marketed under the trademark "NFD Ultrafine ZnO" by Daikin (ZnO coated with phosphate of perfluoroalkyl and a copolymer based on perfluoroalkylethyl as a dispersion in cyclopentasiloxane);
those marketed under the trademark "SPD-Z1" by Shin-Etsu (ZnO coated with a silicone-grafted acrylic polymer dispersed in cyclodimethylsiloxane);
those marketed under the trademark "Escalol Z100" by ISP (alumina-treated ZnO dispersed in an ethylhexyl methoxycinnamate/PVP-hexadecene copolymer/methicone mixture); and
those marketed under the trademark "Fuji ZnO-SMS-10" by Fuji Pigment (ZnO coated with silica and polymethylsilsesquioxane); those marketed under the trademark "Nanox Gel TN" by Elementis (ZnO dispersed at 55% in $C_{12}$-$C_{15}$ alkyl benzoate with hydroxystearic acid polycondensate).

The uncoated cerium oxide pigments are marketed, for example, under the trademark "Colloidal Cerium Oxide" by Rhone-Poulenc.

The uncoated iron oxide pigments are, for example, marketed by Arnaud under the trademarks "Nanogard WCD 2002 (FE 45B)", "Nanogard Iron FE 45 BLAQ", "Nanogard FE 45R AQ" and "Nanogard WCD 2006 (FE 45R)", or by Mitsubishi under the trademark "TY-220".

The coated iron oxide pigments are, for example, marketed by Arnaud under the trademarks "Nanogard WCD 2008 (FE 45B FN)", "Nanogard WCD 2009 (FE 45B 556)", "Nanogard FE 45 BL 345" and "Nanogard FE 45 BL" or by BASF under the trademark "Oxyde de fer transparent".

Mention may also be made of mixtures of metal oxides, in particular of titanium dioxide and of cerium dioxide, including a mixture of equal weights of titanium dioxide coated with silica and of cerium dioxide coated with silica marketed by Ikeda under the trademark "Sunveil A", and also a mixture of titanium dioxide and of zinc dioxide coated with alumina, with silica and with silicone, such as the product "M 261" marketed by Kemira, or coated with alumina, with silica and with glycerol, such as the product "M 211" marketed by Kemira.

Coated inorganic solid UV filters are preferable, because the UV filtering effects of the inorganic solid UV filters can be enhanced. In addition, the coating(s) may function as a binder for fixing the UV filters on a small core particle.

If the inorganic solid UV filter(s) in the form of fine particles is/are used, the composite pigment used in the present invention has an effect of not providing a white appearance but a transparent or clear appearance, because the fine particles of the inorganic solid UV filters do not aggregate but spread on the core particle. It should be noted that free fine particles of inorganic solid UV filter(s) easily aggregate to give a white appearance to the skin.

The inorganic solid UV filter(s) may be used in the composite pigment in proportions such that the weight ratio of the small core particle(s) to the inorganic solid UV filter(s) is from 10:90 to 90:10, preferably from 30:70 to 70:30, and more preferably from 40:60 to 50:50.

(Particulate Organic Solid UV Filter)

As described above, the coating layer on the small core particle may comprise at least one particulate organic solid UV filter. If two or more particulate organic solid UV filters are used, they may be the same or different, preferably the same. The term "UV filters" may be paraphrased with "UV screening agents".

The particulate organic solid UV filter used for the present invention may be active in the UV-A and/or UVB region, preferably in the UV-A region or in the UV-A and UVB region. The particulate organic solid UV filter may be hydrophilic and/or lipophilic.

<<Particulate organic solid UV filter>>, means an organic molecule which (1) is under the form of solid particles at 25° C. and insoluble in the medium of the composition of the invention and (2) which allow by absorption, and/or reflection and/or diffusion of the UVA and/or UVB radiations allows to block or at least to limit the contact of the said radiations with the surface of keratinic materials (skin, hair, scalp).

The term "solid" means solid at 25° C. under 1 atm.

The particulate organic solid UV filters used in the present invention have preferentially a mean particle size which varies from 10 to 5 µm and more preferably from 10 nm to 2 µm and more particularly from 20 nm to 2 µm.

The particulate organic solid UV filters used in the present invention can be brought to the desired particulate form by any ad hoc means, such as, in particular, dry milling or milling in a solvent medium, sieving, atomization, micronization or spraying.

An example of a process for the micronization of insoluble particulate organic UV filters is disclosed in Applications GB-A-2303549 and EP-A-893119, which are incorporated by reference to form an integral part of the description. The milling device used according to these documents can be an airjet mill, bead mill, vibration mill or hammer mill and preferably a mill with high-speed stirring or an impact mill and more particularly a rotary bead mill, a vibrating mill, a tube mill or a rod mill.

The composite pigment used in the present invention has an effect that of providing a transparent or clear appearance, because the fine particles of the particulate organic solid UV filter(s) do not aggregate but spread on the core particle. It should be noted that free fine particles of particulate organic solid UV filter(s) can easily aggregate.

The material of the particulate organic solid UV filter(s) is not limited as long as it is organic. If two or more particulate organic solid UV filters are used, the material(s) of the particulate organic solid UV filters may be the same as or different from each other.

The particulate solid organic UV screening agents used in the present invention can be chosen in particular from particulate organic UV screening agents of the oxalanilide type, of the triazine type, of the benzotriazole type; of the vinyl amide type; of the cinnamamide type; of the type comprising one or more benzazole and/or benzofuran or benzothiophene groups or of the indole type; of the aryl vinylene ketone type; of the phenylenebis(benzoxazinone) derivative type; or of the acrylonitrile amide, sulphonamide or carbamate derivative type.

In the sense in which it is used in the present invention, the term benzazole simultaneously encompasses benzothiazoles, benzoxazoles and benzimidazoles.

Mention may be made, among UV screening agents, of the oxalanilide type in accordance with the invention, of those corresponding to the structure:

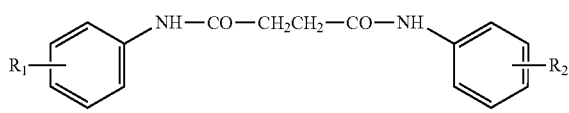
(1)

in which $R_1$ and $R_2$, independently, are $C_1$-$C_{18}$ alkyl or $C_1$-$C_{18}$ alkoxy. A preferred compound of formula (1) is N-(2-ethoxyphenyl)-N'-(2-ethylphenyl)-ethanediamide. These compounds are disclosed in Patent Application WO 95/22959.

Mention may be made, as examples, of the commercial products Tinuvin 315 and Tinuvin 312, sold by Ciba-Geigy, with the respective structures:

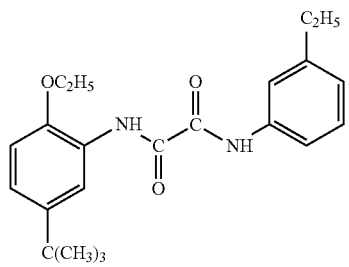

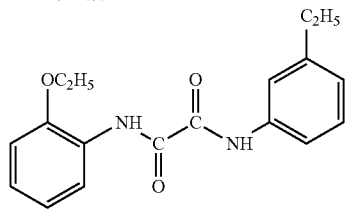

A preferred class of solid triazine UV absorbers is that having the formula:

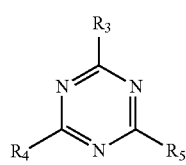
(2)

in which $R_3$, $R_4$ and $R_5$, independently, are H, OH, $C_1$-$C_{18}$ alkoxy, $NH_2$, NH—$R_6$ or $N(R_6)_2$ in which $R_6$ is $C_1$-$C_{18}$ alkyl, $OR_6$ in which $R_6$ is $C_1$-$C_{18}$ alkyl, phenyl, phenoxy or anilino, or pyrrole, in which the respective phenyl, phenoxy or anilino, or pyrrolo moieties are optionally substituted by one, two or three substituents selected from OH, carboxy, CO—$NH_2$, $C_1$-$C_{18}$ alkyl or alkoxy, $C_1$-$C_{18}$ carboxyalkyl, $C_5$-$C_8$ cycloalkyl, a methylidenecamphor group, the group —(CH=CH)$_m$C(=O)—$OR_6$ in which m is 0 or 1 and $R_6$ has the same meaning as above, or the group

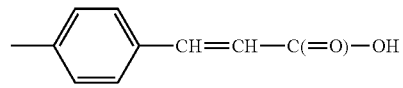

or the corresponding alkali metal, ammonium, mono-, di- or tri-$C_1$-$C_4$ alkylammonium, mono-, di- or tri-$C_2$-$C_4$ alkanolammonium salts, or the $C_1$-$C_{18}$ alkyl esters thereof.

These compounds are disclosed in WO 97/03642, GB 2286774, EP 743309, WO 98/22447 and GB 2319523 (which are incorporated by reference as an integral part of the content of the description).

Preferred compounds of formula (2) are those having one of the formulae:

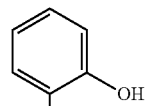
(3)

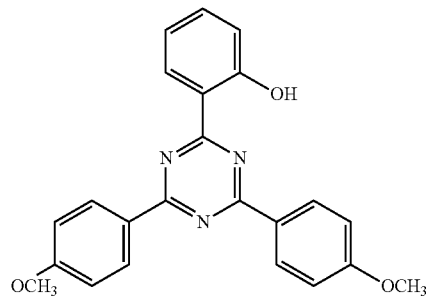

(4)

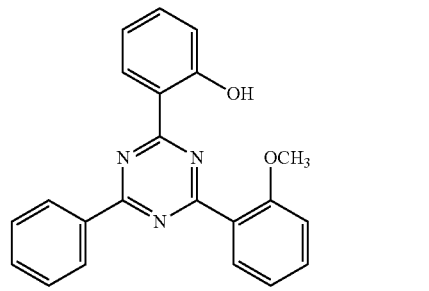

(5)

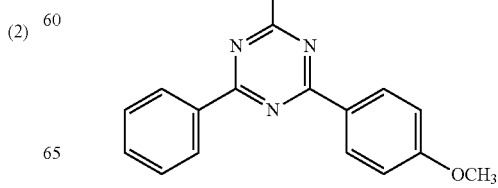

-continued
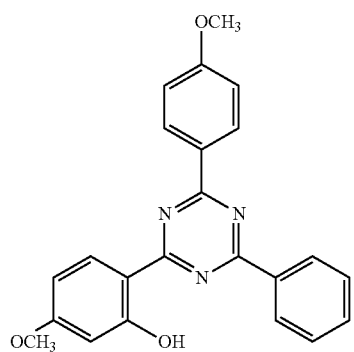
(6)
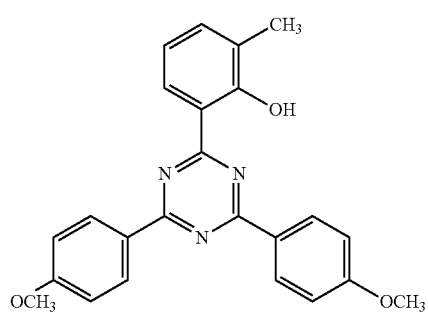
(7)
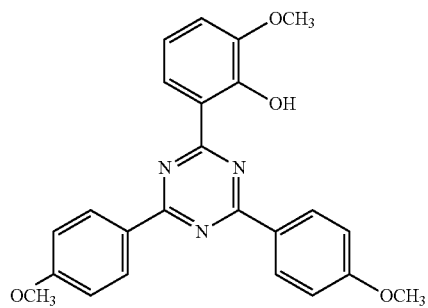
(8)
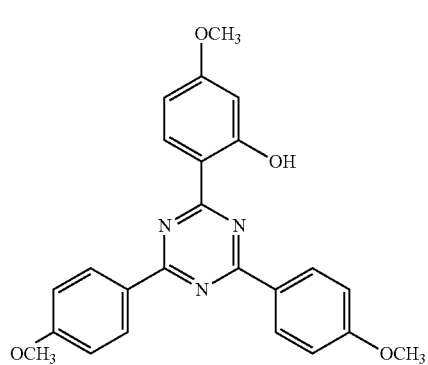
(9)
-continued
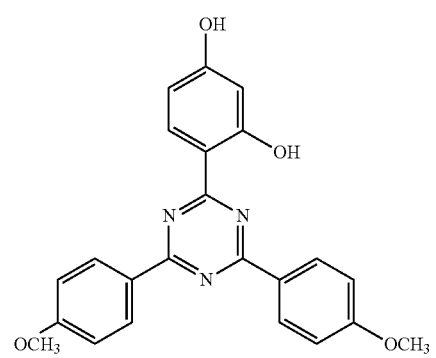
(10)
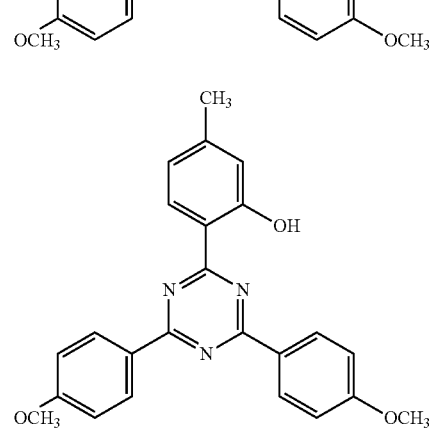
(11)
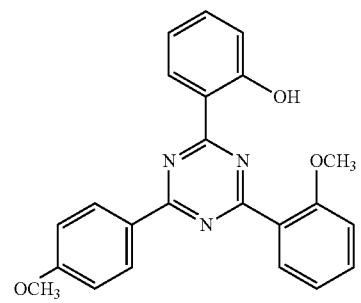
(12)
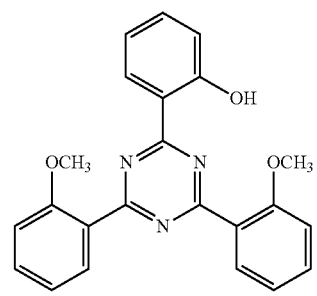
(13)
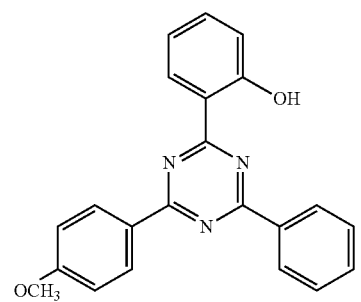
(14)

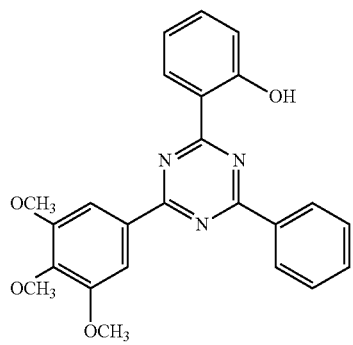
(15)
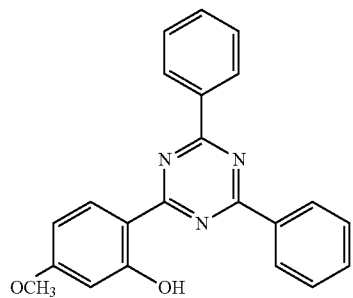
(16)
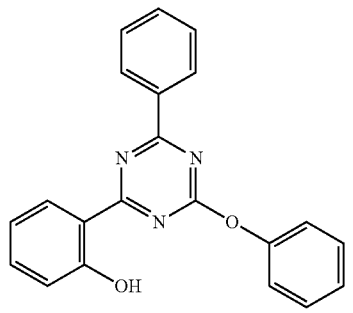
(17)
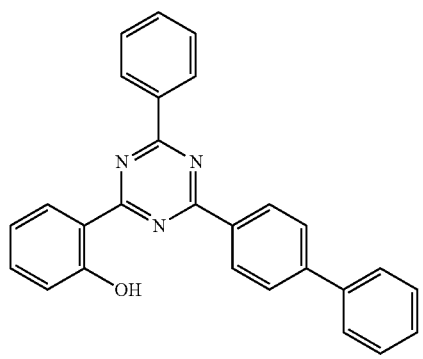
(18)
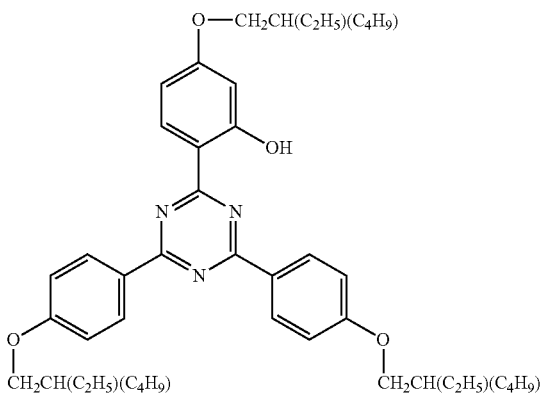
(19)
(20)
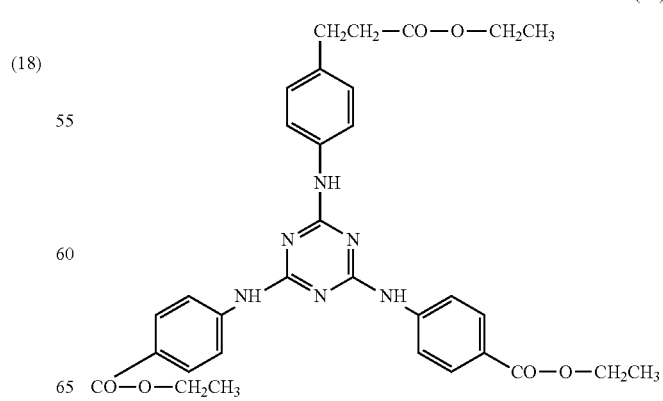
(21)

(22)
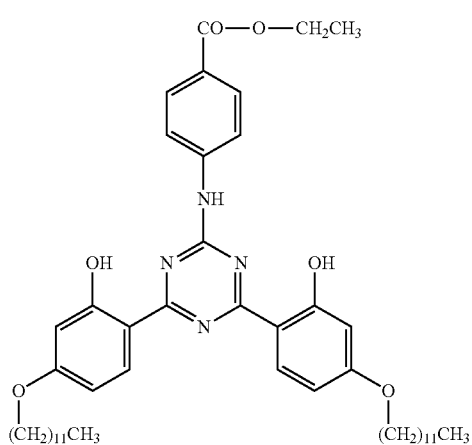
(23)
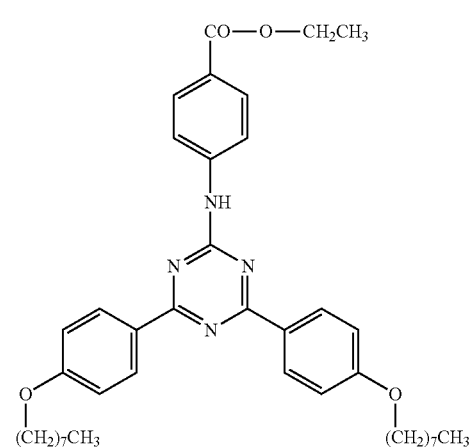
(24)
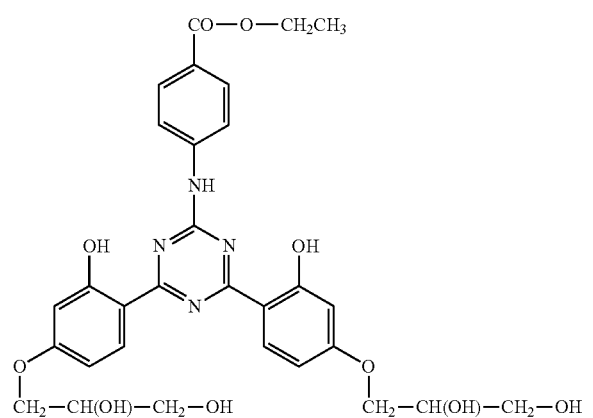
(25)
(26)
(27)
(28)
and as well as 2,4,6-tris(diisobutyl-4'-aminobenzalmalonate)-s-triazine and 2,4-bis(diisobutyl-4-aminobenzalmalonate)-6-(4'-aminobenzylidenecamphor)-s-triazine. Bisethylhexyloxyphenol methoxyphenyl triazine, marketed under the trademark "Tinosorb S" by Ciba-Geigy is in particular preferable.

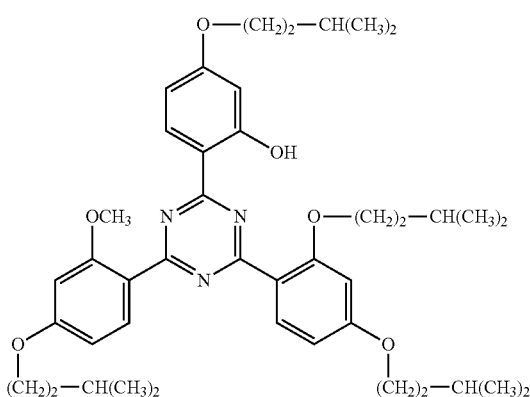

(29)

Particularly preferred compounds of formula (2) are those having the formula:

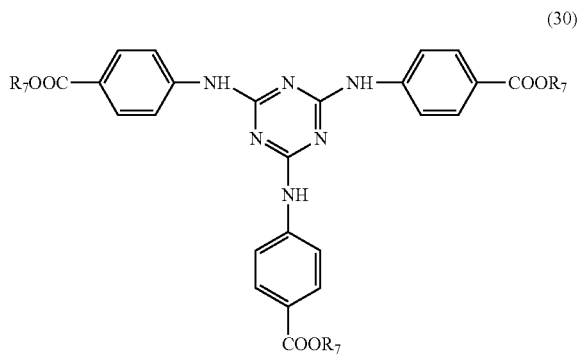

(30)

in which the individual radicals $R_7$ are the same or different and each is hydrogen; an alkali metal; an ammonium group $N(R_8)_4$ in which $R_8$ is hydrogen or an organic radical; $C_1$-$C_{20}$ alkyl; or a polyoxyethylene radical which contains from 1 to 10 ethylene oxide units and the terminal OH group of which may be etherified by a $C_1$-$C_3$ alcohol.

In relation to the compounds of formula (30), when $R_7$ is an alkali metal it is preferably potassium or, especially sodium; when $R_7$ is the group $N(R_8)_4$ in which $R_8$ has its previous meaning, it is preferably a mono-, di- or tri-$C_1$-$C_4$ alkylammonium salt, a mono-, di- or tri-$C_2$-$C_4$ alkanolammonium salt or a $C_1$-$C_{20}$ alkyl ester thereof; when $R_8$ is a $C_1$-$C_{20}$ alkyl group, it is preferably a $C_6$-$C_{12}$ alkyl group, more preferably a $C_8$-$C_9$ alkyl group, especially a 3,5,5-trimethylpentyl group or, most particularly, a 2-ethylhexyl group; and when $R_8$ is a polyoxyethylene group, this preferably contains from 2-6 ethylene oxide units.

Mention may also be made, among UV screening agents of the triazine type in accordance with the invention, of insoluble s-triazine derivatives carrying benzalmalonate and/or phenylcyanoacrylate groups, such as those disclosed in Application EP-A-0 790 243 (which is incorporated by reference as an integral part of the content of the description).

Mention will more particularly be made, among these insoluble UV screening agents of the triazine type, of the following compounds:
2,4,6-tris(diethyl 4'-aminobenzalmalonate)-s-triazine,
2,4,6-tris(diisopropyl 4'-aminobenzalmalonate)-s-triazine,
2,4,6-tris(dimethyl 4'-aminobenzalmalonate)-s-triazine,
2,4,6-tris(ethyl α-cyano-4-aminocinnamate)-s-triazine.

Mention may also be made, among UV screening agents of the triazine type in accordance with the invention, of insoluble s-triazine derivatives carrying benzotriazole and/or benzothiazole groups, such as those disclosed in Application WO 98/25922 (which is incorporated by reference to forms an integral part of the content of the description).

Mention may more particularly be made, among these compounds, of:
2,4,6-tris[(3'-(benzotriazol-2-yl)-2'-hydroxy-5'-methyl)phenylamino]-s-triazine,
2,4,6-tris[(3'-(benzotriazol-2-yl)-2'-hydroxy-5'-tert-octyl)phenylamino]-s-triazine.

A preferred class of solid (benzo)triazole UV absorbers is that having the formula:

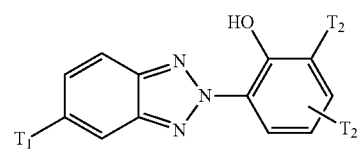

(31)

in which $T_1$ is $C_1$-$C_{18}$ alkyl or, preferably, hydrogen; and $T_2$ is hydrogen, hydroxyl, or $C_1$-$C_{18}$ alkyl, optionally substituted by $C_1$-$C_{12}$ cycloalkyl or an aryl such as phenyl, preferably α,α-dimethylbenzyl. The $C_1$-$C_{18}$ alkyl groups can be linear or branched and are, for example, methyl, ethyl, n-propyl, isopropyl, n-butyl, isobutyl, tert-butyl, tert-octyl, n-amyl, n-hexyl, n-heptyl, n-octyl, isooctyl, n-nonyl, n-decyl, n-undecyl, n-dodecyl, tetradecyl, hexadecyl or octadecyl; the $C_5$-$C_{12}$ cycloalkyl groups are, for example, cyclopentyl, cyclohexyl or cyclooctyl; and the aryl groups are, for example, phenyl or benzyl.

Mention may be made, as examples of compounds of formula (31), of the commercial products Tinuvin 328, 320, 234 and 350 from Ciba-Geigy, with the following structures:

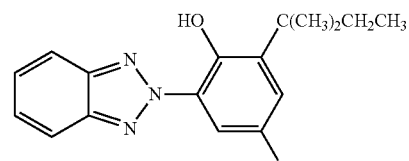

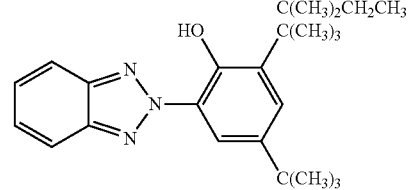

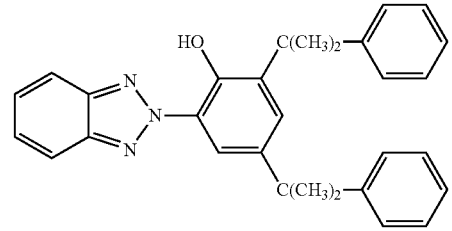

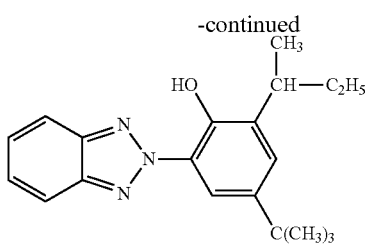

Mention may be made, among insoluble organic UV screening agents of the benzotriazole type in accordance with the invention, of the compounds as disclosed in U.S. Pat. Nos. 5,687,521, 5,373,037 and 5,362,881 and in particular[2,4'-dihydroxy-3-(2H-benzotriazol-2-yl)-5-(1,1,3,3-tetramethylbutyl)-2'-(n-octoxy)-5'-benzoyl]diphenylmethane, sold under the name Mixxim PB30 by Fairmount Chemical, with the structure:

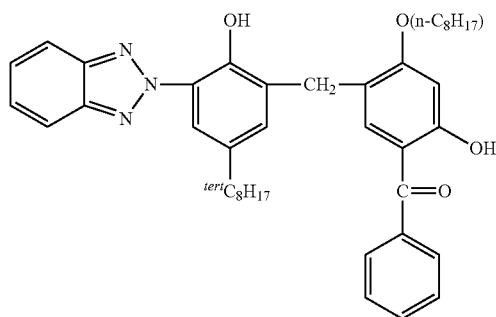

A further preferred class of solid (benzo)triazole UV absorbers is that having the formula:

(32)

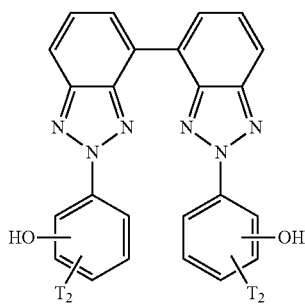

in which $T_2$ has its previous meaning.

A still further preferred class of solid triazole UV absorbers is that having the formula:

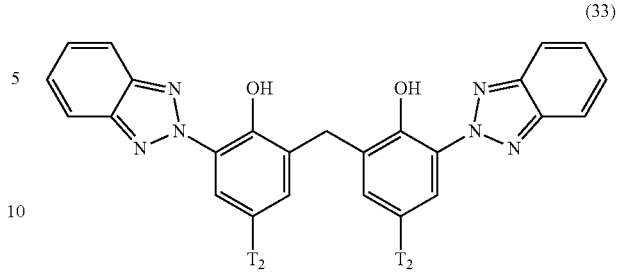

in which $T_2$ has its previous meaning and is preferably methyl, t-butyl or —$C(CH_3)_2$—$CH_2$—$C(CH_3)_3$. Thus, preferred solid triazole UV absorbers are as follows.

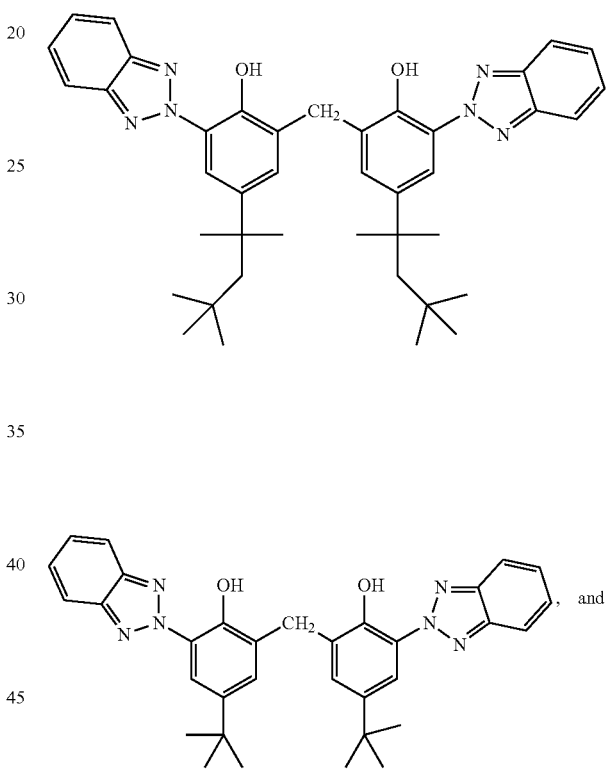

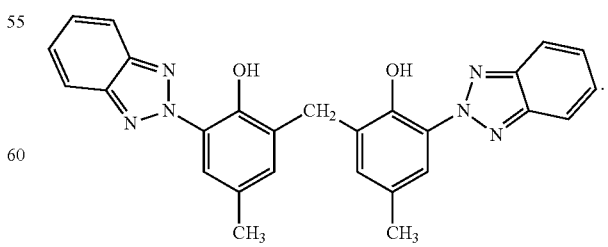

More particulary, the particulate organic solid UV filter will be the molecule of formula

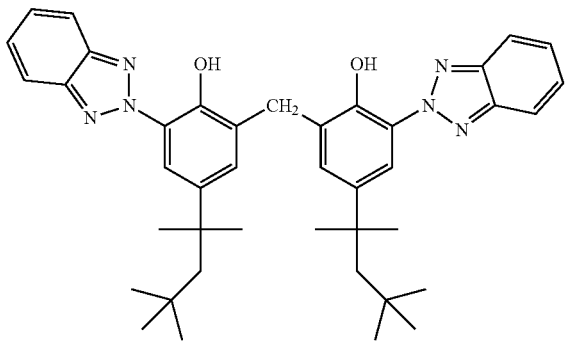 [SMILES: CC(C)(C)CC(C)(C)c1cc(Cc2cc(C(C)(C)CC(C)(C)C)cc(-n3nc4ccccc4n3)c2O)c(O)c(-n2nc3ccccc3n2)c1]

with the nomenclature 2,2'-methylenebis[6-(2H-benzotriazol-2-yl)-4-(1,1,3,3-tetramethylbutyl)phenol], and the INCI Name: METHYLENE BIS-BENZOTRIAZOLYL TETRAMETHYLBUTYLPHENOL as for instance sold under the commercial name TINOSORB M from the company BASF or MIXXIM BB100 from Fairmount Chemical.

A preferred class of solid vinyl group-containing amide UV absorbers is that having the formula:

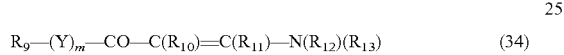 (34)

in which $R_9$ is $C_1$-$C_{18}$ alkyl, preferably $C_1$-$C_5$ alkyl, or phenyl optionally substituted by one, two or three substituents selected from OH, $C_1$-$C_{18}$ alkyl, $C_1$-$C_{18}$ alkoxy or CO—$OR_6$ in which $R_6$ has its previous meaning; $R_{10}$, $R_{11}$, $R_{12}$ and $R_{13}$ are the same or different and each is $C_1$-$C_{18}$ alkyl, preferably $C_1$-$C_5$ alkyl, or hydrogen; Y is N or O; and m has its previous meaning.

Preferred compounds of formula (34) are 4-octyl-3-penten-2-one, ethyl-3-octylamino-2-butenoate, 3-octylamino-1-phenyl-2-buten-1-one and 3-dodecylamino-1-phenyl-2-buten-1-one.

A preferred class of solid cinnamic acid amide UV absorbers is that having the formula:

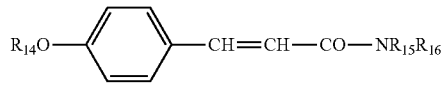 (35)

in which $R_{14}$ is hydroxy or $C_1$-$C_4$ alkoxy, preferably methoxy or ethoxy; $R_{15}$ is hydrogen or $C_1$-$C_4$ alkyl, preferably methyl or ethyl; and $R_{16}$ is —(CONH)$_m$-phenyl in which m has its previous meaning and the phenyl group is optionally substituted by one, two or three substituents selected from OH, $C_1$-$C_{18}$ alkyl, $C_1$-$C_{18}$ alkoxy or CO—$OR_6$ in which $R_6$ has its previous meaning. Preferably $R_{16}$ is phenyl, 4-methoxyphenyl or the phenylaminocarbonyl group.

Mention may also be made of cinnamamide dimers, such as those disclosed in U.S. Pat. No. 5,888,481, such as, for example, the compound with the structure:

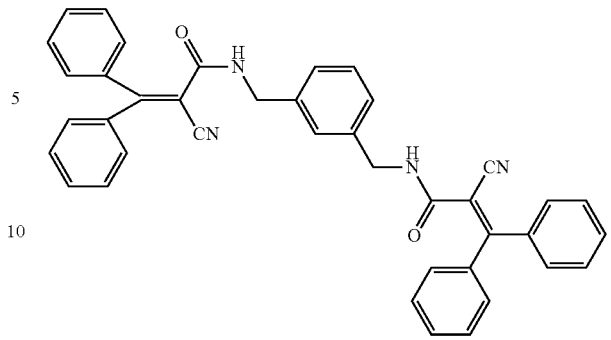

The compounds of formula (1) to (35) are known. The compounds of formula (30) are described, together with their production, in U.S. Pat. No. 4,617,390.

It is preferable that the particulate organic solid UV filter(s) be a benzotriazole derivative, in particular, a phenylbenzotriazole derivative such as a drometrizole trisiloxane, marketed under the trademark "Silatrizole" by Rhodia Chimie or "Mexoryl XL" by L'Oreal, as represented below.

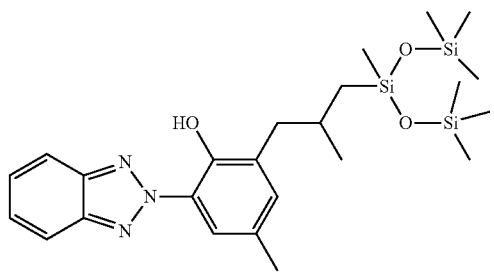 [SMILES: Cc1cc(CC(C)C[Si](C)(O[Si](C)(C)C)O[Si](C)(C)C)c(O)c(-n2nc3ccccc3n2)c1]

Mention may be made, among insoluble organic screening agents of the benzazole type, of those corresponding to one of the following formulae:

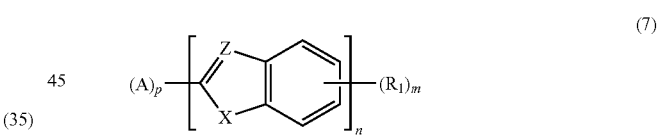 (7)

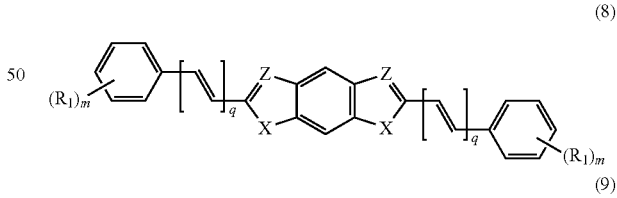 (8)

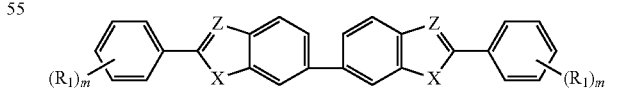 (9)

in which each of the X symbols independently represents an oxygen or sulphur atom or an $NR_2$ group,
each of the Z symbols independently represents a nitrogen atom or a CH group,
each of the $R_1$ symbols independently represents an OH group, a halogen atom, a linear or branched $C_{1-8}$ alkyl group, optionally comprising a silicon atom, or a linear or branched $C_{1-8}$ alkoxy group, each of the numbers m independently has the value 0, 1 or 2, n represents an integer between 1 and 4 inclusive, p is equal to 0 or 1, each of the numbers q is independently equal to 0 or 1, each of the $R_2$ symbols independently represents a hydrogen atom or a benzyl or linear or branched $C_{1-8}$ alkyl group, optionally comprising a silicon atom, A represents a radical with a valency n chosen from those of formulae:

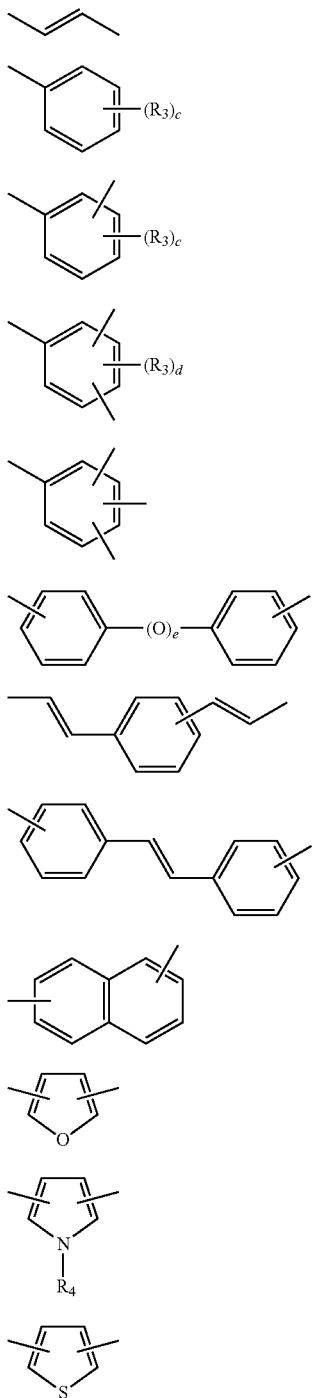

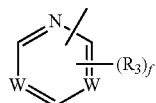

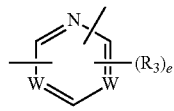

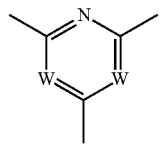

in which W denotes N or CH; each of the $R_3$ symbols independently represents a halogen atom or a linear or branched $C_{1-4}$ alkyl or alkoxy group or a hydroxyl group, $R_4$ represents a hydrogen atom or a linear or branched $C_{1-4}$ alkyl group, c=0-4, d=0-3, e=0 or 1 and f=0-2.

These compounds are disclosed in particular in Patents DE 676 103 and CH 350 763, U.S. Pat. Nos. 5,501,850, 5,961,960, Patent Application EP 0 669 323, U.S. Pat. Nos. 5,518,713, 2,463,264, the paper in J. Am: Chem. Soc., 79, 5706-5708, 1957, the paper in J. Am. Chem. Soc., 82, 609-611, 1960, Patent Application EP 0 921 126 and Patent Application EP 712 855.

Mention may be made, as examples of preferred compounds of formula (7) of the family of the 2-arylbenzazoles, of 2-(benzoxazol-2-yl)-4-methylphenol, 2-(1H-benzimidazol-2-yl)-4-methoxyphenol or 2-(benzothiazol-2-yl)phenol, it being possible for these compounds to be prepared, for example, according to the processes disclosed in Patent CH 350 763.

Mention will be made, as examples of preferred compounds of formula (7) of the family of the benzimidazolylbenzazoles, of 2,2'-bisbenzimidazole, 5,5',6,6'-tetramethyl-2,2'-bisbenzimidazole, 5,5'-dimethyl-2,2'-bisbenzimidazole, 6-methoxy-2,2'-bisbenzimidazole, 2-(1H-benzimidazol-2-yl)benzothiazole, 2-(1H-benzimidazol-2-yl)benzoxazole and N,N'-dimethyl-2,2'-bisbenzimidazole, it being possible for these compounds to be prepared according to the procedures disclosed in U.S. Pat. Nos. 5,961,960 and 2,463,264.

Mention will be made, as examples of preferred compounds of formula (7) of the family of the phenylenebenzazoles, of 1,4-phenylenebis(2-benzoxazolyl), 1,4-phenylenebis(2-benzimidazolyl), 1,3-phenylenebis(2-benzoxazolyl), 1,2-phenylenebis(2-benzoxazolyl), 1,2-phenylenebis(benzimidazolyl), 1,4-phenylenebis(N-(2-ethylhexyl)-2-benzimidazolyl) and 1,4-phenylenebis(N-trimethylsilylmethyl-2-benzimidazolyl), it being possible for these compounds to be prepared according to the procedures disclosed in U.S. Pat. No. 2,463,264 and in the publications J. Am. Chem. Soc., 82, 609 (1960) and J. Am. Chem. Soc., 79, 5706-5708 (1957).

Mention will be made, as examples of preferred compounds of formula (7) of the family of the benzofuranylbenzoxazoles, of 2-(2-benzofuranyl)benzoxazole, 2-(benzofuranyl)-5-methylbenzoxazole and 2-(3-methyl-2-benzofuranyl)benzoxazole, it being possible for these compounds to be prepared according to the procedures disclosed in U.S. Pat. No. 5,518,713.

Mention may be made, as preferred compounds of formula (8), of, for example, 2,6-diphenyl-1,7-dihydrobenzo[1,2-d; 4,5-d']diimidazole, corresponding to the formula:

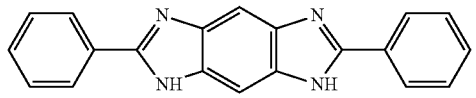

or 2,6-distyryl-1,7-dihydrobenzo[1,2-d; 4,5-d']diimidazole or 2,6-di(p-tert-butylstyryl)-1,7-dihydrobenzo[1,2-d; 4,5-d']diimidazole, which compounds can be prepared according to Application EP 0 669 323.

Mention may be made, as preferred compound of formula (9), of 5,5'-bis(2-phenylbenzimidazole) of formula:

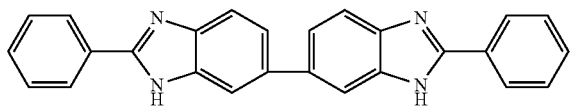 [SMILES: c1ccc(-c2nc3ccc(-c4ccc5nc(-c6ccccc6)[nH]c5c4)cc3[nH]2)cc1]

the preparation of which is described in J. Chim. Phys., 64, 1602 (1967).

Preference is very particularly given, among these solid organic compounds which screen out UV radiation, to 2-(1H-benzimidazol-2-yl)benzoxazole, 6-methoxy-2,2'-bisbenzimidazole, 2-(1H-benzimidazol-2-yl)benzothiazole, 1,4-phenylenebis(2-benzoxazolyl), 1,4-phenylenebis(2-benzimidazolyl), 1,3-phenylenebis(2-benzoxazolyl), 1,2-phenylenebis(2-benzoxazolyl), 1,2-phenylenebis(2-benzimidazolyl) and 1,4-phenylenebis(N-trimethylsilylmethyl-2-benzimidazolyl).

Mention may be made, among solid organic screening agents of the aryl vinylene ketone type, of those corresponding to either of the following formulae (10) and (11):

(10)

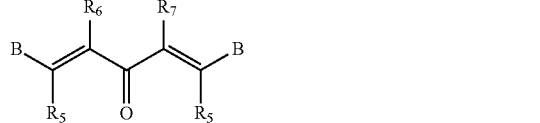
(11)

in which:
n'=1 or 2,
B, in the formula (10) when n'=1 or in the formula (11), is an aryl radical chosen from the following formulae (a') to (d') or, in the formula (10) when n'=2, is a radical chosen from the following formulae (e') to (h'):

(a')

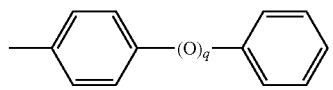
(b')

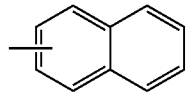
(c')

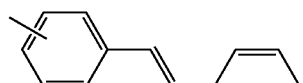
(d')

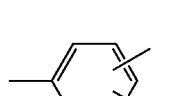
(e')

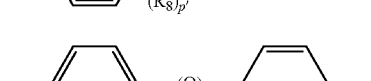
(f')

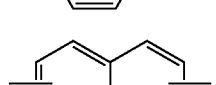
(g')

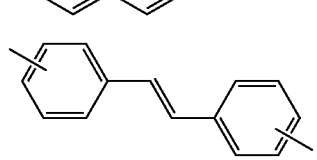
(h')

in which:
each of the $R_8$ symbols independently represents an OH group, a halogen atom, a linear or branched $C_{1-6}$ alkyl group optionally comprising a silicon atom, a linear or branched $C_{1-6}$ alkoxy group optionally comprising a silicon atom, a linear or branched $C_{1-5}$ alkoxycarbonyl group, or a linear or branched $C_{1-6}$ alkylsulphonamide group optionally comprising a silicon atom or an amino acid functional group,
p' represents an integer between 0 and 4 inclusive,
q' represents 0 or 1,
$R_5$ represents hydrogen or an OH group,
$R_6$ represents hydrogen, a linear or branched $C_{1-6}$ alkyl group optionally comprising a silicon atom, a cyano group, a $C_{1-6}$ alkylsulphonyl group or a phenylsulphonyl group,
$R_7$ represents a linear or branched $C_{1-6}$ alkyl group optionally comprising a silicon atom or a phenyl group which can form a bicycle and which is optionally substituted by one or two $R_4$ radicals,
or $R_6$ and $R_7$ together form a monocyclic, bicyclic or tricyclic $C_{2-10}$ hydrocarbonaceous residue, optionally interrupted by one or more nitrogen, sulphur and oxygen atoms and which can comprise another carbonyl, and optionally substituted by a linear or branched $C_1$-$C_8$ alkylsulphonamide group, and optionally comprising a silicon atom or an amino acid functional group; provided that, when n'=1, $R_6$ and $R_7$ do not form a camphor nucleus.

Mention may be made, as examples of compounds of formula (10) in which n'=1, which screen out UV radiation and which have a mean particle size of between 10 nm and 5 μm, of the following families;
compounds of the styryl ketone type as disclosed in Application JP 04 134 042, such as 1-(3,4-dimethoxyphenyl)-4,4-dimethylpent-1-en-3-one:

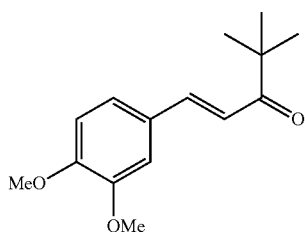 [SMILES: COc1ccc(/C=C/C(=O)C(C)(C)C)cc1OC]

compounds of the benzylidenecineole type, such as those described in the article by E. Mariani et al., 16th IFSCC Congress, New York (1990), for example 1,3,3-trimethyl-5-(4-methoxybenzylidene)-2-oxabicyclo[2.2.2]octan-6-one:

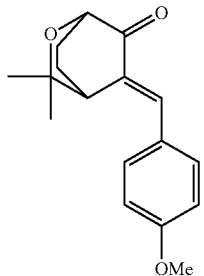 [SMILES: COc1ccc(/C=C2/C(=O)C3CCC2C(C)(C)O3)cc1]

compounds of the benzylidenechromanone type, such as those disclosed in Application JP 04 134 043, for example 3-(4-methoxybenzylidene)-2,3,4a,8a-tetrahydrochromen-4-one:

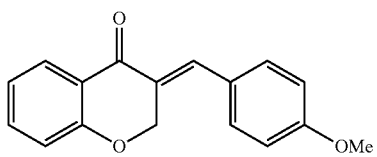 [SMILES: COc1ccc(/C=C2\COc3ccccc3C2=O)cc1]

compounds of the benzylidenethiochromanone type, such as those disclosed in Application JP 04 134 043, for example 3-(4-methoxybenzylidene)-2,3,4a,8a-tetrahydrochromen-4-thione:

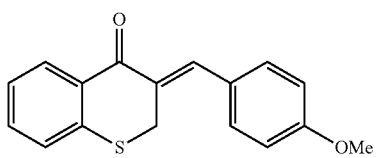 [SMILES: COc1ccc(/C=C2\CSc3ccccc3C2=O)cc1]

compounds of the benzylidenequinuclidinone type, such as those disclosed in Application EP 0 576 974, for example 4-methoxybenzylidene-1-azabicyclo[2.2.2]octan-3-one:

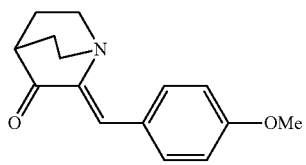 [SMILES: COc1ccc(/C=C2/C(=O)C3CCN2CC3)cc1]

compounds of the benzylidenecycloalkanone type, such as those disclosed in Application FR 2 395 023, for example 2-(4-methoxybenzylidene)cyclopentanone and 2-(4-methoxybenzylidene)cyclohexanone:

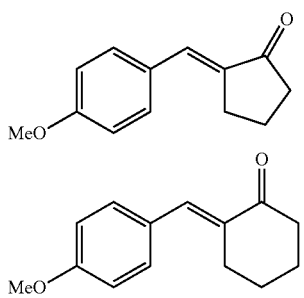

compounds of the benzylidenehydantoin type, such as those disclosed in Application JP 01 158 090, for example 5-(3,4-dimethoxybenzylidene)imidazolidine-2,4-dione:

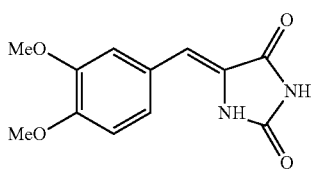 [SMILES: COc1ccc(/C=C2\NC(=O)NC2=O)cc1OC]

compounds of the benzylideneindanone type, such as those disclosed in Application JP 04 134 043, for example 2-(4-methoxybenzylidene)indan-1-one:

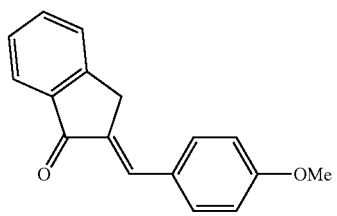 [SMILES: COc1ccc(/C=C2\Cc3ccccc3C2=O)cc1]

compounds of the benzylidenetetralone type, such as those disclosed in Application JP 04 134 043, for example 2-(4-methoxybenzylidene)-3,4-dihydro-2H-naphthalen-1-one;

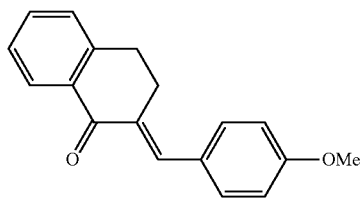 [SMILES: COc1ccc(/C=C2\CCc3ccccc3C2=O)cc1]

compounds of the benzylidenefuranone type, such as those disclosed in Application EP 0 390 683, for example 4-(4-methoxybenzylidene)-2,2,5,5-tetramethyldihydrofuran-3-one:

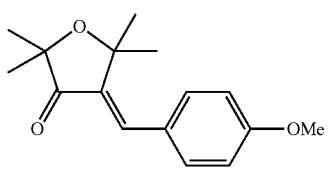 [SMILES: COc1ccc(/C=C2/C(=O)C(C)(C)OC2(C)C)cc1]

compounds of the benzylidenebenzofuranone type, such as those disclosed in Application JP 04 134 041, for example 2-benzylidenebenzofuran-3-one:

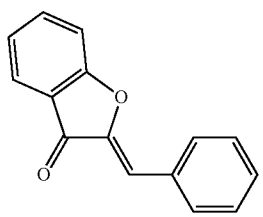 [SMILES: O=C1/C(=C/c2ccccc2)Oc2ccccc21]

compounds of the benzylideneindanedione type, such as 2-(3,5-di(tert-butyl)-4-hydroxybenzylidene)indane-1,3-dione:

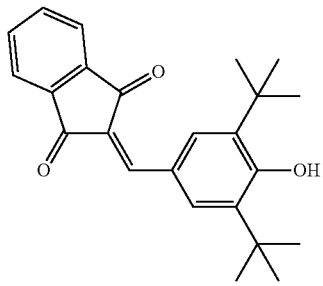 [SMILES: CC(C)(C)c1cc(C=C2C(=O)c3ccccc3C2=O)cc(C(C)(C)C)c1O]

compounds of the benzylidenebenzothiofuranone type, such as those disclosed in Application JP 04,134,043, for example 2-benzylidenebenzo[b]thiophen-3-one:

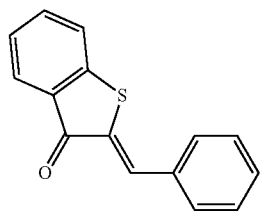 [SMILES: O=C1/C(=C/c2ccccc2)Sc2ccccc21]

compounds of the benzylidenebarbituric type, such as 5-(4-methoxybenzylidene)-1,3-dimethylpyrimidine-2,4,6-trione:

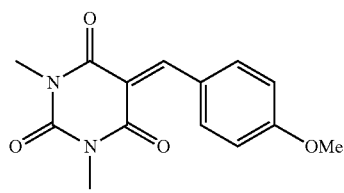 [SMILES: COc1ccc(C=C2C(=O)N(C)C(=O)N(C)C2=O)cc1]

compounds of the benzylidenepyrazolone type, such as 4-(4-methoxybenzylidene)-5-methyl-2-phenyl-2,4-dihydropyrazol-3-one:

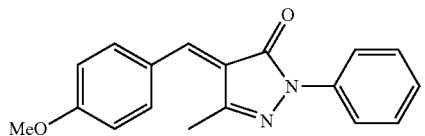 [SMILES: COc1ccc(/C=C2/C(=O)N(c3ccccc3)N=C2C)cc1]

compounds of the benzylideneimidazolone type, such as 5-(4-methoxybenzylidene)-2-phenyl-3,5-dihydroimidazol-4-one:

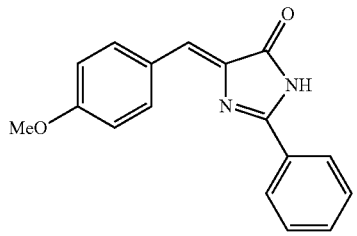 [SMILES: COc1ccc(/C=C2\N=C(c3ccccc3)NC2=O)cc1]

compounds of the chalcone type, such as 1-(2-hydroxy-4-methoxyphenyl)-3-phenylpropenone:

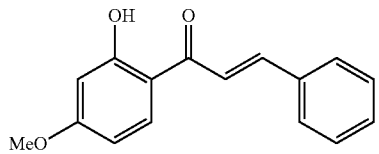 [SMILES: COc1ccc(C(=O)/C=C/c2ccccc2)c(O)c1]

benzylidenone compounds as disclosed in the document FR 2 506 156, for example 3-hydroxy-1-(2-hydroxy-4-methoxyphenyl)-3-phenylpropenone:

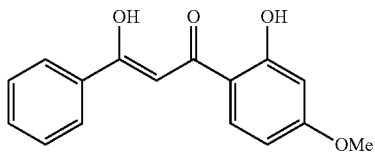 [SMILES: COc1ccc(C(=O)/C=C(\O)c2ccccc2)c(O)c1]

Mention may be made, as examples of compounds of formula (10) in which n'=2, which are insoluble, which screen out UV radiation and which have a mean particle size of between 10 nm and 5 μm, of the following families:

compounds of the phenylenebis(methylidenenorcamphor) type as disclosed in the document EP 0 693 471, for example 1,4-phenylenebis{3-methylidenebicyclo[2.2.1]heptan-2-one}:

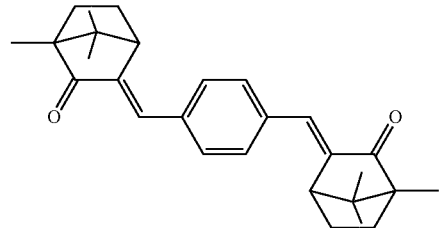

or 1,3-phenylenebis{3-methylidene-1,7,7-trimethylbicyclo[2.2.1]heptan-2-one}:

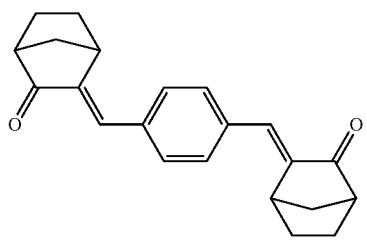 [SMILES: O=C1/C(=C/c2ccc(/C=C3/C(=O)C4CCC3C4)cc2)C2CCC1C2]

compounds of the phenylenebis(methylidenecamphor) type as disclosed in the document FR 2 528 420, for example 1,4-phenylenebis {3-methylidene-1,7,7-trimethylbicyclo[2.2.1]heptan-2-one}:

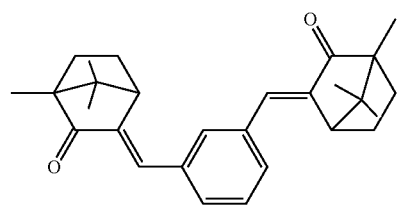

compounds of the phenylenebis(methylidenecamphorsulphonamide) type, such as those disclosed in the document FR 2 529 887, for example 1,4-phenylenebis{3,3'-methylidenecamphor-10,10'-ethylsulphonamide or (2-ethylhexyl)sulphonamide}:

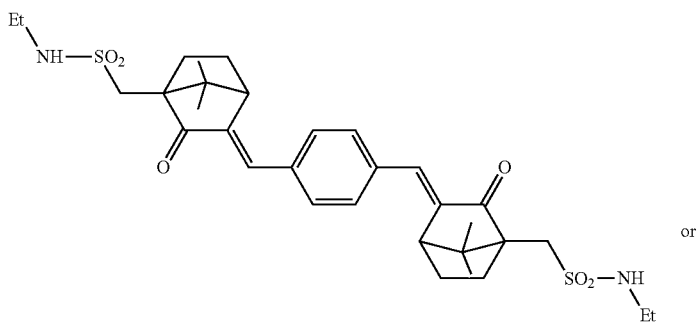

or

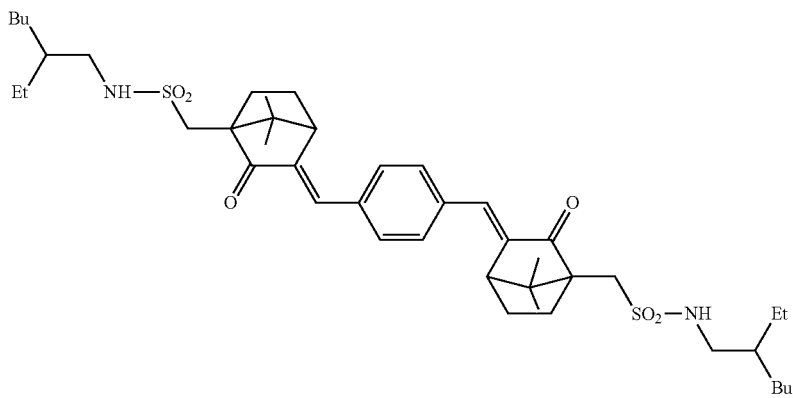

compounds of the phenylenebis(methylidenecineole) type as described in the paper by E. Mariani et al., 16th IFSCC Congress, New York (1990), for example 1,4-phenylenebis{5-methylidene-3,3-dimethyl-2-oxabicyclo[2.2.2]octan-6-one}:

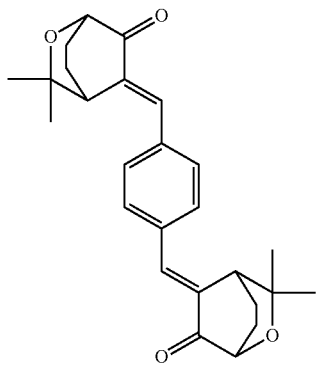

compounds of the phenylenebis(methylideneketotricyclodecane) type as disclosed in Application EP 0 694 521, such as 1,4-phenylenebis(octahydro-4,7-methano-6-inden-5-one):

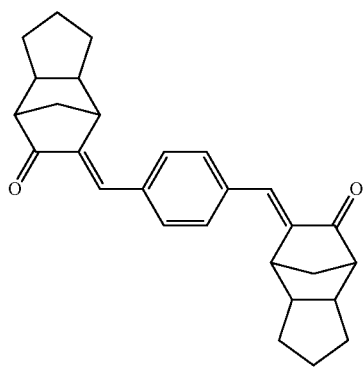 [SMILES: O=C1/C(=C/c2ccc(/C=C3/C(=O)C4CC3C3CCCC43)cc2)C2CC1C1CCCC21]

compounds of the phenylenebis(alkylene ketone) type, such as those disclosed in Application JP 04 134 041, for example 1,4-phenylenebis(4,4-dimethylpent-1-en-3-one):

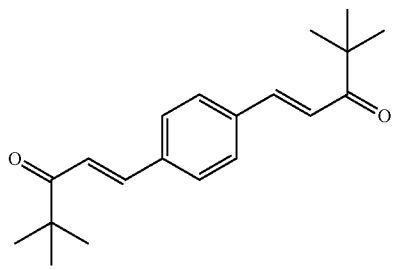 [SMILES: CC(C)(C)C(=O)/C=C/c1ccc(/C=C/C(=O)C(C)(C)C)cc1]

compounds of the phenylenebis(methylidenefuranone) type as disclosed in Application FR 2 638 354, for example 1,4-phenylenebis(4-methylidene-2,2,5,5-tetramethyldihydrofuran-3-one):

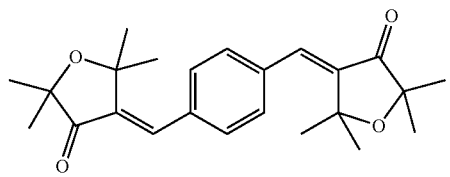

compounds of the phenylenebis(methylidenequinuclidinone) type, such as those disclosed in Application EP 0 714 880, for example 1,4-phenylenebis {2-methylidene-1-azabicyclo[2.2.2]octan-3-one}:

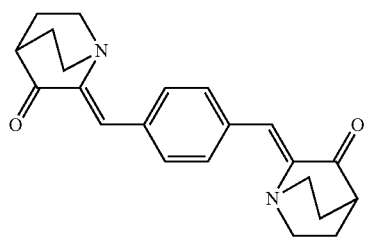 [SMILES: O=C1/C(=C/c2ccc(/C=C3/C(=O)C4CCN3CC4)cc2)N2CCC1CC2]

Mention may be made, as compounds of formula (11), of the following families:

compounds of the bis(benzylidene)cycloalkanone type, such as 2,5-di(benzylidene)cyclopentanone:

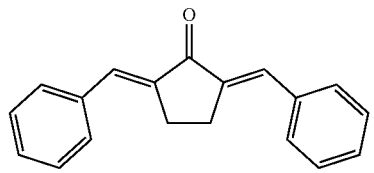 [SMILES: O=C1/C(=C/c2ccccc2)CC/C1=C\c1ccccc1]

compounds of the γ-pyrone type as disclosed in the document JP 04 290 882, for example 2,6-bis(3,4-dimethoxyphenyl)pyran-4-one:

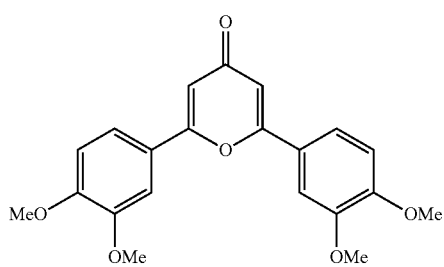 [SMILES: COc1ccc(-c2cc(=O)cc(-c3ccc(OC)c(OC)c3)o2)cc1OC]

Preference is very particularly given, among these insoluble organic compounds which screen out UV radiation of the aryl vinylene ketone type, to the compounds of formula (10) in which n'=2.

Mention may be made, among solid organic screening agents of the phenylenebis(benzoxazinone) type, of those corresponding to the following formula (12):

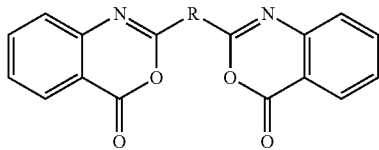

(12)

with R representing a divalent aromatic residue chosen from the following formulae (e″) to (h″):

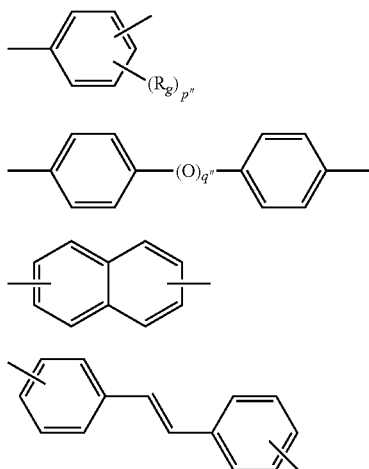

in which:
each of the $R_9$ symbols independently represents an OH group, a halogen atom, a linear or branched $C_{1-6}$ alkyl group optionally comprising a silicon atom, a linear or branched $C_{1-6}$ alkoxy group optionally comprising a silicon atom, a linear or branched $C_{1-5}$ alkoxycarbonyl group, or a linear or branched $C_{1-6}$ alkylsulphonamide group optionally comprising a silicon atom or an amino acid functional group,
p″ represents an integer between 0 and 4 inclusive,
q″ represents 0 or 1.

Mention may be made, as examples of compounds of formula (12), which are insoluble, which screen out UV radiation and which have a mean particle size of between 10 nm and 5 μm, of the following derivatives:
2,2′-p-phenylenebis(3,1-benzoxazin-4-one), commercial product Cyasorb UV-3638 from Cytec,
2,2′-(4,4′-biphenylene)bis(3,1-benzoxazin-4-one),
2,2′-(2,6-naphthylene)bis(3,1-benzoxazin-4-one).

Mention may be made, among solid organic screening agents of the acrylonitrile amide, sulphonamide or carbamate derivative type, of those corresponding to the following formula (13):

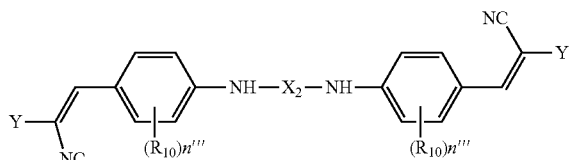

(13)

in which:
$R_{10}$ represents a linear or branched $C_{1-8}$ alkyl group,
n′ has the value 0, 1 or 2,
$X_2$ represents a divalent radical of formula —(C=O)—$R_{11}$—(C=O)—, —$SO_2$—$R_{11}$—$SO_2$— or —(C=O)—O—$R_{11}$—O—(C=O)—,
Y represents a —(C=O)—$R_{12}$ or —$SO_2R_{13}$ radical,
$R_{11}$ represents a single bond or a linear or branched, divalent $C_1$-$C_{30}$ alkylene or $C_3$-$C_{30}$ alkenylene radical which can carry one or more hydroxyl substituents and which can comprise, in the carbonaceous chain, one or more heteroatoms chosen from oxygen, nitrogen and silicon atoms,
$R_{12}$ represents an —$OR_{14}$ or —$NHR_{14}$ radical,
$R_{13}$ represents a linear or branched $C_1$-$C_{30}$ alkyl radical or a phenyl ring which is unsubstituted or substituted by $C_1$-$C_4$ alkyl or alkoxy radicals,
$R_{14}$ represents a linear or branched $C_1$-$C_{30}$ alkyl or $C_3$-$C_{30}$ alkenyl radical which can carry one or more hydroxyl substituents and which can comprise, in the carbonaceous chain, one or more heteroatoms chosen from oxygen, nitrogen and silicon atoms.

Although only the isomers in which the cyano substituent is in the cis position with respect to the para-aminophenyl substituent are represented in the above formula (13), this formula should be understood as also encompassing the corresponding trans isomers; for each of the two double bonds, and independently, the cyano and para-aminophenyl substituents can be in the cis or trans configuration with respect to one another.

Mention may be made, as example, of the dimer of 2-ethylhexyl 2-cyano-3[4-(acetylamino)phenyl]acrylate of formula:

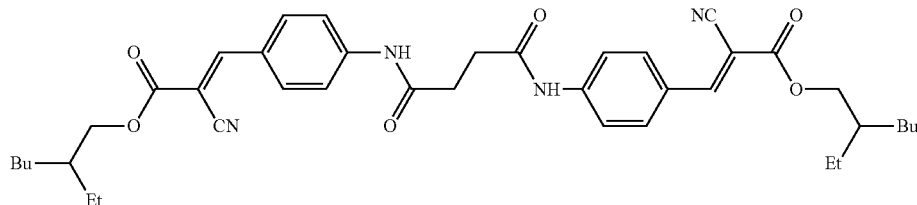

Another specific family of solid organic screening agents in accordance with the invention are the polyvalent metal salts (for example, $Ca^{2+}$, $Zn^{2+}$, $Mg^{2+}$, $Ba^{2+}$, $Al^{3+}$ or $Zr^{4+}$) of sulphonic or carboxylic organic screening agents, such as the polyvalent metal salts of sulphonated derivatives of benzylidenecamphor, such as those disclosed in Application FR-A 2 639 347; the polyvalent metal salts of sulphonated derivatives of benzimidazole, such as those disclosed in Application EP-A-893 119; or the polyvalent metal salts of cinnamic acid derivatives, such as those disclosed in Application JP-87 166 517.

Mention may also be made of metal or ammonium or substituted ammonium complexes of UV-A and/or UVB organic screening agents as disclosed in Patent Applications WO 93/10753, WO 93/11095 and WO 95/05150.

A preferred class of particulate solid sulfonated benzimidazole UV absorbers is that having the formula:

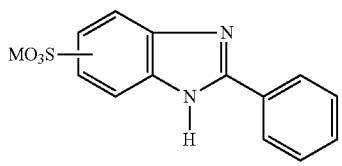

(36)

in which M is hydrogen or an alkali metal, preferably sodium, an alkaline earth metal, such as magnesium or calcium, or zinc.

In the compounds of formula (1) to (35), $C_1$-$C_{18}$ alkyl groups may be methyl, ethyl, n-propyl, isopropyl, n-butyl, isobutyl, tert-butyl, n-amyl, n-hexyl, n-heptyl, n-octyl, iso-octyl, n-nonyl, n-decyl, n-undecyl, n-dodecyl, tetradecyl, hexydecyl or octadecyl; and $C_1$-$C_{18}$ alkoxy groups include methoxy, ethoxy, propoxy, butoxy, n-hexoxy, n-heptoxy, n-octoxy, iso-octoxy, n-nonoxy, n-decoxy, n-undecoxy, n-dodecoxy, tetradecoxy, hexadecoxy or octadecoxy, methoxy and ethoxy being preferred.

$C_1$-$C_{18}$ carboxyalkyl includes carboxymethyl, carboxyethyl, carboxypropyl, carboxylsopropyl, carboxybutyl, carboxylsobutyl, carboxybutyl, carboxyamyl, carboxyhexyl, carboxyheptyl, carboxyoctyl, carboxylsooctyl, carboxynonyl, carboxydecyl, carboxyundecyl, carboxydodecyl, carboxytetradecyl, carboxyhexadecyl and carboxyoctadecyl, carboxymethyl being preferred.

$C_5$-$C_8$ cycloalkyl includes cyclopentyl, cyclohexyl and cyclooctyl.

The particulate organic solid UV filter may be selected from the group consisting of benzotriazole, derivatives, oxanilide derivatives, triazine derivatives, triazole derivatives, vinyl-group containing amides, cinnamic acid amides, and sulfonated benzimidazoles.

It is also preferable that the particulate organic solid UV filter(s) is selected from methylenebis(hydroxyphenylbenzotriazole) derivatives in the form of a solid.

Methylene bis-benzotriazolyl tetramethylbutylphenol, such as 2,2'-methylenebis[6-(2H-benzotriazol-2-yl)-4-methyl-phenol] marketed in the solid form under the trademark "Mixxim BB/200" by Fairmount Chemical, or 2,2'-methylenebis[6-(2H-benzotriazol-2-yl)-4-(1,1,3,3-tetramethylbutyl)phenol] marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071, 5,166,355, GB-2,303,549, DE-197,26, 184 and EP-893,119, are in particular preferable.

The particulate organic solid UV filter(s) may be used in the composite pigment in proportions such that the weight ratio of the small core particle to the particulate organic solid UV filter(s) is from 10:90 to 90:10, preferably from 30:70 to 80:20, and more preferably from 40:60 to 50:50.

(Coloring Pigment)

As described above, the coating layer(s) on the small core particle may comprise at least one coloring pigment.

The term "coloring pigment(s)" should be understood as meaning white or colored, inorganic or organic particle(s) of any shape which is/are insoluble and is/are intended to color a composition comprising them.

If coloring pigment(s) is/are used, the composite pigment has an effect of providing a clearer appearance with high chroma, because the coloring pigments do not aggregate but spread on the substrate. It should be noted that free coloring pigments easily aggregate to give a dark appearance with low chroma to the skin. Therefore, the color of the cosmetics including coloring pigments can be opaque and dark. On the other hand, the composite pigment according to the present invention can provide clear and bright color tone.

The pigments can be white or colored, inorganic and/or organic and generally have a mean particle size greater or equal to 1 µm.

Among the inorganic pigments that may be used, non-limiting mention may be made of titanium dioxide, optionally surface treated, zirconium or cerium oxide, as well as zinc, (black, yellow or red) iron or chromium oxide, manganese violet, ultramarine blue, chromium hydrate and ferric blue, barium sulfate, or metal powders, such as aluminum, copper, silver or gold powder.

The particle size of the coloring pigment is not limited. In a particular embodiment, the coloring pigment may have a mean particle size of from 100 nm to less than 1 µm, preferably from 100 nm to less than 500 nm, and more preferably from 100 nm to less than 300 nm.

Since particles of coloring pigment(s) can be firmly bonded on the small core particle, the coloring pigment(s) cannot penetrate into the skin via pores on the skin. In addition, even if the coloring pigment(s) irritate, a large amount of the coloring pigment(s) cannot directly contact with the skin, because they are present only on the small core particle. Accordingly, the composite pigment according to the present invention is safer than the bulk of coloring pigments.

Among organic pigments that may be used, non-limiting mention may be made of carbon black, pigments of D&C type and lakes, such as lakes-based on cochineal carmine and on barium, strontium, calcium or aluminum. For example, Red 202 (Calcium bis[2-(3-carboxy-2-hydroxy-nephthylazo)-5-methylbenzenesulfonate) may be used as the pigment of D&C type.

Preferably, the coloring pigment is chosen from titanium dioxide, zirconium oxide, cerium oxide, zinc oxide, iron oxide, chromium oxide, manganese violet, ultramarine blue, chromium hydrate, ferric blue, aluminum powder, copper powder, silver powder, gold powder, barium sulfate, carbon black, pigments of D&C type, lakes, pearlescent pigments, and mixtures thereof.

The term "pearlescent pigments" should be understood as meaning iridescent particles of any shape, such as particles produced by certain shellfish in their shells or else synthesized.

The pearlescent agents can be chosen from white pearlescent agents, such as mica covered with titanium dioxide or with bismuth oxychloride; colored pearlescent agents, such as titanium oxide-coated mica covered with iron oxide, titanium oxide-coated mica covered with ferric blue or chromium oxide, or titanium oxide-coated mica covered with an organic pigment of the abovementioned type; and pearlescent agents based on bismuth oxychloride.

The composite pigment used in the present invention can provide a better feeling on use, because fine particles of coloring pigment(s), if used, can be firmly fixed on the small core particles so that it is possible to reduce free fine particles which have a high friction coefficient such that they do not easily spread on the skin and provide an unpleasant feeling on use.

The coloring pigment(s) may be used in the composite pigment in proportions such that the weight ratio of the small core particle to the coloring pigment(s) is from 50:50 to 90:10, preferably from 50:50 to 80:20, and more preferably from 50:50 to 70:30.

(Additional UV Filter)

As described above, the coating layer on the small core particle may further comprise at least one additional UV filter. If two or more additional UV filters are used, they may be the same or different, preferably the same.

The additional UV filter used for the present invention may be active in the UV-A and/or UV-B region, preferably in the UV-A region or in the UV-A and UV-B region. The additional UV filter may be hydrophilic and/or lipophilic.

The additional UV filter may be solid or liquid, preferably liquid. The terms "solid" and "liquid" mean solid and liquid, respectively, at 25° C. under 1 atm. The additional UV filter may be made from at least one organic or inorganic material, preferably at least one organic material.

The additional UV filter(s) may be selected from the group consisting of anthranilic derivatives; dibenzoylmethane derivatives; cinnamic derivatives; salicylic derivatives; camphor derivatives; benzophenone derivatives; β,β-diphenylacrylate derivatives; triazine derivatives; benzotriazole derivatives; benzalmalonate derivatives; benzimidazole derivatives; imidazoline derivatives; bis-benzoazolyl derivatives; p-aminobenzoic acid (PABA) and derivatives thereof; methylenebis(hydroxyphenylbenzotriazole) derivatives; benzoxazole derivatives; screening polymers and screening silicones; dimers derived from α-alkylstyrene; 4,4-diarylbutadienes; octocrylene and derivatives thereof, guaiazulene and derivatives thereof, rutin and derivatives thereof, flavonoids, biflavonoids, oryzanol and derivatives thereof, quinic acid and derivatives thereof, phenols, retinol, cysteine, aromatic amino acids, peptides having an aromatic amino acid residue, and mixtures thereof.

Mention may be made, as examples of the additional organic UV filter(s), of those denoted below under their INCI names, and mixtures thereof.

Anthranilic derivatives: Menthyl anthranilate, marketed under the trademark "Neo Heliopan MA" by Haarmann and Reimer.

Dibenzoylmethane derivatives: Butyl methoxydibenzoylmethane, marketed in particular under the trademark "Parsol 1789" by Hoffmann-La Roche; and isopropyl dibenzoylmethane.

Cinnamic derivatives: Ethylhexyl methoxycinnamate, marketed in particular under the trademark "Parsol MCX" by Hoffmann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate.

Salicylic derivatives: Homosalate (homomentyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer.

Camphor derivatives, in particular, benzylidenecamphor derivatives: 3-benzylidene camphor, manufactured under the trademark "Mexoryl SD" by Chimex; 4-methylbenzylidene camphor, marketed under the trademark "Eusolex 6300" by Merck; benzylidene camphor sulfonic acid, manufactured under the trademark "Mexoryl SL" by Chimex; camphor benzalkonium methosulfate, manufactured under the trademark "Mexoryl SO" by Chimex; terephthalylidene dicamphor sulfonic acid, manufactured under the trademark "Mexoryl SX" by Chimex; and polyacrylamidomethyl benzylidene camphor, manufactured under the trademark "Mexoryl SW" by Chimex.

Benzophenone derivatives: Benzophenone-1 (2,4-dihydroxybenzophenone), marketed under the trademark "Uvinul 400" by BASF; benzophenone-2 (Tetrahydroxybenzophenone), marketed under the trademark "Uvinul D50" by BASF; Benzophenone-3 (2-hydroxy-4-methoxybenzophenone) or oxybenzone, marketed under the trademark "Uvinul M40" by BASF; benzophenone-4 (hydroxymethoxy benzophonene sulfonic acid), marketed under the trademark "Uvinul MS40" by BASF; benzophenone-5 (Sodium hydroxymethoxy benzophenone Sulfonate); benzophenone-6 (dihydroxy dimethoxy benzophenone); marketed under the trademark "Helisorb 11" by Norquay; benzophenone-8, marketed under the trademark "Spectra-Sorb UV-24" by American Cyanamid; benzophenone-9 (Disodium dihydroxy dimethoxy benzophenonedisulfonate), marketed under the trademark "Uvinul DS-49" by BASF; benzophenone-12, and n-hexyl 2-(4-diethylamino-2-hydroxybenzoyl)benzoate.

β,β-Diphenylacrylate derivatives: Octocrylene, marketed in particular under the trademark "Uvinul N539" by BASF; and Etocrylene, marketed in particular under the trademark "Uvinul N35" by BASF.

Triazine derivatives: diethylhexyl butamido triazone, marketed under the trademark "Uvasorb HEB" by Sigma 3V; 2,4,6-tris(dineopentyl 4'-aminobenzalmalonate)-s-triazine.

Benzotriazole derivatives, in particular, phenylbenzotriazole derivatives:

2-(2H-benzotriazole-2-yl)-6-dodecyl-4-methylpheno, branched and linear; and those described in U.S. Pat. No. 5,240,975.

Benzalmalonate derivatives: Dineopentyl 4'-methoxybenzalmalonate, and polyorganosiloxane comprising benzalmalonate functional groups, such as polysilicone-15, marketed under the trademark "Parsol SLX" by Hoffmann-LaRoche.

Benzimidazole derivatives, in particular, phenylbenzimidazole derivatives: Phenylbenzimidazole sulfonic acid, marketed in particular under the trademark "Eusolex 232" by Merck, and disodium phenyl dibenzimidazole tetrasulfonate, marketed under the trademark "Neo Heliopan AP" by Haarmann and Reimer.

Imidazoline derivatives: Ethylhexyl dimethoxybenzylidene dioxoimidazoline propionate.

Bis-benzoazolyl derivatives: The derivatives as described in EP-669,323 and U.S. Pat. No. 2,463,264.

Para-aminobenzoic acid and derivatives thereof: PABA (p-aminobenzoic acid), ethyl PABA, Ethyl dihydroxypropyl PABA, pentyl dimethyl PABA, ethylhexyl dimethyl PABA, marketed in particular under the trademark "Escalol 507" by ISP, glyceryl PABA, and PEG-25 PABA, marketed under the trademark "Uvinul P25" by BASF.

Benzoxazole derivatives:
2,4-bis[5-1(dimethylpropyl)benzoxazol-2-yl-(4-phenyl)imino]-6-(2-ethylhexyl)imino-1,3,5-triazin e, marketed under the trademark of Uvasorb K2A by Sigma 3V.

Screening polymers and screening silicones: The silicones described in WO 93/04665.

Dimers derived from α-alkylstyrene: The dimers described in DE-19855649.

4,4-Diarylbutadiene derivatives: 1,1-dicarboxy(2,2'-dimethylpropyl)-4,4-diphenylbutadiene.

Quaiazulene and derivatives thereof: Guaiazulene and sodium guaiazulene sulfonate.

Rutin and derivatives thereof: Rutin and glucosylrutin.

Flavonoids: Robustin (isoflavonoid), genistein (flavonoid), tectochrysin (flavonoid), and hispidone (flavonoid).

Biflavonoids: Lanceolatin A, lanceolatin B, and hypnumbiflavonoid A.

Oryzanol and derivatives thereof: F-oryzanol.

Quinic acid and derivatives thereof: Quinic acid.

Phenols: Phenol.

Retinols: Retinol.

Cysteines: L-cysteine.

Peptides having an aromatic amino acid residue: Peptides having tryptophan, tyrosine or phenylalanine.

The preferred organic additional UV filter(s) is selected from:
butyl methoxydibenzoylmethane, ethylhexyl methoxycinnamate, homosalate, ethylhexyl salicylate, octocrylene, phenylbenzimidazole sulfonic acid, benzophenone-3, benzophenone-4, benzophenone-5, n-hexyl 2-(4-diethylamino-2-hydroxybenzoyl)benzoate, 4-methylbenzylidene camphor, terephthalylidene dicamphor sulfonic acid, disodium phenyl dibenzimidazole tetrasulfonate, ethylhexyl triazone, bis-ethylhexyloxyphenol methoxyphenyl triazine, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, methylene bis-benzotriazolyl tetramethylbutylphenol, polysilicone-15, dineopentyl 4'-methoxybenzalmalonate, 1,1-dicarboxy(2,2'-dimethylpropyl)-4,4-diphenylbutadiene, 2,4-bis[5-1(dimethylpropyl)benzoxazol-2-yl-(4-phenyl)imino]-6-(2-ethylhexyl)imino-1,3,5-triazin e, and their mixtures. A more preferable organic UV filter is butyl methoxydibenzoylmethane (Avobenzone).

In a preferred embodiment, the additional UV filter is an organic liquid IN filter.

The material of the organic liquid UV filter(s) is not limited as long as it is organic. If two or more organic liquid UV filters are used, the material(s) of the organic liquid UV filters may be the same as or different from each other.

Amongst the liquid additional organic UV filter, we can mention:

Cinnamic derivatives: Ethylhexyl methoxycinnamate, marketed in particular under the trademark "Parsol MCX" by Hoffmann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate.

Salicylic derivatives: Homosalate (homomentyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer.

β,β-Diphenylacrylate derivatives: Octocrylene, marketed in particular under the trademark "Uvinul N539" by BASF; and Etocrylene, marketed in particular under the trademark "Uvinul N35" by BASF.

Polyorganosiloxane comprising benzalmalonate functional groups, such as polysilicone-15, marketed under the trademark "Parsol SLX" by Hoffmann-LaRoche.

The preferred organic liquid additional UV filter(s) may be selected from:
ethylhexyl methoxycinnamate, homosalate, ethylhexyl salicylate, octocrylene, polysilicone-15.

The additional UV filter(s) may be used in the composite pigment in proportions such that the weight ratio of the small core particle to the additional UV filter(s) is from 50:50 to 90:10, preferably from 50:50 to 80:20, and more preferably from 50:50 to 70:30.

(Large Core Particle)

The composite pigment used in the present invention may further comprise at least one large core particle. It is preferable that the composite pigment comprise at least one large core particle.

The large core particle to be used for the composite pigment is not limited, as long as the large core particle has a mean particle size or a mean particle diameter of 2 μm or more, preferably 3 μm or more, more preferably 4 μm or more, and even more preferably 5 μm or more. The mean particle size of the large core particle may be limited to 50 μm or less, preferably 30 μm or less, and more preferably 20 μm or less, and even more preferably 10 μm or less.

The mean particle size or mean particle diameter here is an arithmetic mean diameter, and can be determined, for example, by calculating the average of the dimensions of one hundred particles chosen on an image obtained with a scanning electron microscope.

The large core particle may be hollow or solid. It may be preferable to use solid large particle.

The large particle can be in any shape. For example, it is possible to use a large particle in the form of a plate with an aspect ratio of at least 5, preferably more than 10, more preferably more than 20, and more preferably more than 50. The aspect ratio can be determined by the average thickness and the average length according to the formula: aspect ratio=length/thickness.

If a plate-like particle is used for the present invention, it is preferable that the plate-like particle have a length ranging from 2 μm or more, preferably 3 μm or more, more preferably 4 μm or more, and even more preferably 5 μm or more, to 50 μm or less, preferably 30 μm or less, and more preferably 20 μm or less, and even more preferably 10 μm or less.

In a preferred embodiment, the large core particle has a spherical shape.

The material of the large core particle is not limited. The material can be at least one inorganic material and/or at least one organic material, preferably at least one organic material.

The inorganic material and/or organic material may be hollow or porous. The porosity of the material may be characterized by a specific surface area of from 0.05 $m^2$/g to 1,500 $m^2$/g, more preferably from 0.1 $m^2$/g to 1,000 $m^2$/g, and more preferably from 0.2 $m^2$/g to 500 $m^2$/g according to the BET method.

Preferably, the inorganic material can be selected from the group consisting of mica, synthetic mica, talc, sericite, boron nitride, glass flakes, calcium carbonate, barium sulfate, titanium oxide, hydroxyapatite, silica, silicate, zinc oxide, magnesium sulfate, magnesium carbonate, magnesium trisilicate, aluminum oxide, aluminum silicate, calcium silicate, calcium phosphate, magnesium oxide, bismuth oxychloride, kaolin, hydrotalcite, mineral clay, synthetic clay, iron oxide, and mixtures thereof. Natural mica, synthetic mica, sericite, kaolin, talc, silica and mixtures thereof are more preferable.

In particular, silica particles such as P-1500 marketed by JGC C&C are preferable as inorganic large particles.

Preferably, the organic material can be selected from the group consisting of poly(meth)acrylates, polyamides, silicones, polyurethanes, polyethylenes, polypropylenes, polystyrenes, copolystyrenes, polyhydroxyalkanoates, polycaprolactams, poly(butylene) succinates, polysaccharides, polypeptides, polyvinyl alcohols, polyvinyl resins, fluoropolymers, waxes, amidosulfonic acid polyvalent metal salts, acylated amino acids, and mixtures thereof. As the fluoropolymers, for example, PTFE may be used. As the amidosulfonic acid polyvalent metal salts, for example, N-lauroyltaurine calcium may be used. As the acylated amino acids, lauroyllysine may be used. Polyamides such as Nylon®, polyhydroxyalkanoates such as polylactic acids, poly(meth) acrylates such as polymethylmethacrylates, silicones, fluoropolymers, and mixtures thereof are more preferable.

In particular, polymethylmethacrylate particles such as MR-7GC marketed by Soken in Japan, polyamide particles such as SP-500 marketed by Toray, Orgasol marketed by Arkema, and PTFE particles such as Ceridust 9205F marketed by Clariant, are preferable as organic large core particles.

The large core particle may or may not be coated beforehand. In a particular embodiment, the large core particle is originally coated. The material of an original coating of the large core particle is not limited, but an organic material such as an amino acid, an N-acylamino acid, an amido, a silicone, a modified silicone and a polyolefin, is preferable. As the organic material, mention may be made of lauroyl lysine, acryl-modified silicone and polyethylene.

In particular, silica particles coated with polyethylene such as ACEMATT OK412 marketed by Degussa may be preferable as coated (inorganic) large particles.

In the composite pigment used in the present invention, the weight ratio of the small core particle(s) to the large core particle(s) may be from 10:90 to 90:10, preferably from 20:80 to 80:20, and more preferably from 30:70 to 70:30.

In a particular embodiment, the weight ratio of the small core particle(s)/the large core particle(s)/the inorganic or organic particulate solid UV filter(s) may be from 20:50:30 to 50:20:30, preferably from 35:15:50 to 15:35:50, and more preferably from 10:20:70 to 20:10:70.

In a preferred embodiment, the weight ratio of the small core particle(s)/the large core particle(s)/the inorganic or organic particulate solid UV filter(s) may be from 50:20:30 or 35:15:50.

In a preferred embodiment, the composite pigment may satisfy the following requirements:
the small particle comprises at least one copolystyrene, preferably a styrene/acrylate copolymer, and/or a cross-linked styrene/methyl methacrylate copolymer;
the large particle comprises at least one poly(meth)acrylate, preferably a methyl methacrylate polymer; and
the small and large particles are at least in part covered with at least one coating layer comprising an inorganic solid UV filter selected from metal oxide such as titanium oxide.

(Method for Preparing Composite Pigment)

One embodiment of the composite pigments used in the present invention can be prepared by subjecting
at least one small particle with a mean particle size more than 100 nm and of less than 1 μm, preferably less than 600 nm, and more preferably less than 400 nm;
at least one inorganic or organic particulate solid UV filter; and
optionally at least one coloring pigment and/or at least one additional UV filter to a mechanochemical fusion process.

Another embodiment of the composite pigment used in the present invention can be prepared by can be obtained by subjecting:
at least one small particle with a mean particle size more than 100 nm and of less than 1 μm, preferably less than 600 nm, and more preferably less than 400 nm;
at least one large particle with a mean particle size of 2 μm or more, preferably 3 μm or more, more preferably 4 μm or more, and even more preferably 5 μm or more;
at least one inorganic or organic particulate solid UV filter; and
optionally at least one coloring pigment and/or at least one additional UV filter to a mechanochemical fusion process.

The small core particle, the large core particle, the inorganic or organic particulate solid UV filter, the coloring pigment, and the additional UV filter are as explained above.

Mechanochemical fusion process means a process in which mechanical power such as impact force, friction force or shear force is applied to a plurality of subjects to cause fusion between the subjects.

The mechanochemical fusion process may be performed by, for example, an apparatus comprising a rotating chamber and a fixed inner piece with a scraper, such as a mechano-fusion system marketed by Hosokawa Micron Corporation in Japan.

It is preferable to use a hybridizer process as the mechanochemical fusion process.

The hybridizer process was developed in the 1980s. The hybridizer process is a class of mechanochemical fusion processes in which strong mechanical power is applied to a plurality of particles to cause a mechanochemical reaction to form a composite particle.

According to the hybridizer process, the mechanical power is imparted by a high-speed rotor which can have a diameter from 10 cm to 1 m, and can rotate at a speed of 1,000 rpm to 100,000 rpm. Therefore, the hybridizer process can be defined as a mechanochemical fusion process using such a high-speed rotor. The hybridizer process is performed in air or under dry conditions. Thus, due to the high-speed rotation of the rotor, high-speed air flow may be generated near the rotor. However, some liquid materials may be subjected to the hybridizer process together with solid materials. The term "hybridizer process" has been used as a technical term.

The hybridizer process can be performed by using a hybridization system marketed by, for example, Nara Machinery in Japan, in which at least two types of particles, typically core particles and fine particles, are fed into a hybridizer equipped with a high-speed rotor having a plurality of blades in a chamber under dry conditions, and the particles are dispersed in the chamber and mechanical and thermal energy (e.g., compression, friction and shear stress) are imparted to the particles for a relatively short period of time such as 1 to 10 minutes, preferably 1 to 5 minutes.

As a result, one type of particles (e.g., fine particles) is embedded or fixed on the other type of particles (e.g., core particle) to form composite particles. It is preferable that the particles have been subjected to electrostatic treatment(s) such as shaking to form an "ordered mixture" in which one type of particles is spread to cover the other type of particles. The hybridizer process can also be performed by using a theta composer marketed by Tokuju Corporation in Japan.

The hybridizer process can also be performed by using a Composi Hybrid or a Mechano Hybrid marketed by Nippon coke.

According to the present invention, for example, small core particles and inorganic or organic particulate solid UV filter(s) as well as optionally additional material(s) such as large core particles, coloring pigment(s) and/or additional UV filter(s) if necessary, can be fed into such a hybridizer to form a composite pigment. The hybridizer process can be performed by using a rotor rotating at about 8,000 rpm (100 m/sec) for about 3 minutes.

If the large core particles are used, the small core particle(s) and the large core particle(s) can be used in proportions such that the weight ratio of the small core particle(s) to the large core particle(s) is from 10:90 to 90:10, preferably from 20:80 to 80:20, and more preferably from 30:70 to 70:30.

In a particular embodiment, the weight ratio of the small core particle(s)/the large core particle(s)/the inorganic or organic particulate solid UV filter(s) may be from 20:50:30 to 50:20:30, preferably from 35:15:50 to 15:35:50, and more preferably from 10:20:70 to 20:10:70.

In a preferred embodiment, the weight ratio of the small core particle(s)/the large core particle(s)/the inorganic or organic particulate solid UV filter(s) may be from 50:20:30 or 35:15:50.

The mechanochemical fusion process, in particular the hybridizer process, enables to provide a composite pigment in which small core particles are at least in part covered by at least one layer comprising at least one inorganic or organic particulate solid UV filter, and optionally at least one large core particle and/or at least one coloring pigment and/or at least one additional UV filter. The surface of the large core particles may also be at least in part covered by at least one layer comprising at least one selected from the group consisting of particulate organic solid UV filters, inorganic solid UV filters, coloring pigments and additional UV filters.

Furthermore, the mechanochemical fusion process, in particular the hybridizer process, can provide ordered array (e.g., uniform coverage) of inorganic or organic particulate solid UV filter(s), and optionally at least one coloring pigment and/or at least one additional UV filter on small core particles (and possible large core particles as well) and provides strong bonds at the surface of the small (and large) core particle and a coating layer comprising the inorganic or organic particulate solid UV filter(s), and optionally coloring pigment(s) and/or additional UV filter(s).

If the large core particles are used in combination with the small core particles, according to the present invention, the inorganic or organic particulate solid UV filter, and optionally the additional UV filter and/or the coloring pigment, can be effectively bound on the surface of the small core particles due to the anchor effects by the collision of the large core particles to the small core particles. Therefore, the UV filtering effects, and optionally coloring effects, can be further enhanced.

It should be noted that the mechanochemical fusion process, in particular the hybridizer process, is quite different from other processes using, for example, a beads mill and a jet mill. In fact, a beads mill causes pulverization or aggregation of core particles, and a jet mill causes pulverization of core particles and uniform coating of a core particle by fine particles is difficult to be formed.

If necessary, an additional process for further coating the composite pigments with UV filter(s) and/or coloring material(s) may be performed. As a result of this additional process, the composite pigment according to the present invention may be coated with a further layer comprising UV filter(s) and/or coloring material(s), preferably consisting of UV filter(s) and/or coloring material(s).

The composite pigment, as described above, can be present in the cosmetic composition according to the present invention in an amount ranging from 0.01% to 99% by weight, preferably from 0.1% to 50% by weight, and more preferably from 1% to 30% by weight, relative to the total weight of the composition.

Preferably, the composite pigment can be used in cosmetic compositions to be applied to keratin substances such as skin, hair, and nails, providing superior UV shielding effects, and optionally coloring effects, because the composite pigment can exhibit good UV filtering effects possibly with a transparent or clear appearance and/or good coloring effects such as more transparent or clearer and more bright coloring, without the risk of affecting keratin substances. Furthermore, the composite pigment according to the present invention is easy to be formulated into and can be stabilized in cosmetic compositions.

Since the composite pigment can reduce free particles which have a high friction coefficient such that they do not easily spread on the skin and provide an unpleasant feeling on use, the cosmetic composition according to the present invention has reduced friction, and therefore, can provide the effect of a better smooth feeling on use.

[Organopolysiloxane Elastomer]

The cosmetic composition according to the present invention comprises at least one organopolysiloxane elastomer.

In a preferred embodiment, the cosmetic composition according to the present invention may comprise a non-emulsifying silicon elastomer.

The non-emulsifying silicon elastomer may be in form of a gel or a powder.

The 'organopolysiloxane elastomer' or 'silicone elastomer' makes it possible to thicken the composition and to improve the application properties thereof. It provides a very soft and mattifying feel after application, which is especially advantageous for an application to the skin. This elastomer is either a gel or a soft powder.

The expression "organopolysiloxane elastomer" or "silicone elastomer" means a flexible, deformable organopolysiloxane having viscoelastic properties and especially the consistency of a sponge or a flexible sphere. Its modulus of elasticity is such that this material withstands deformation and has limited stretchability and contractability. This material is capable of regaining its original shape after stretching.

It is more particularly a crosslinked organopolysiloxane elastomer.

Thus, the organopolysiloxane elastomer may be obtained by crosslinking addition reaction of diorganopolysiloxane containing at least one hydrogen bonded to silicon and of diorganopolysiloxane containing ethylenically unsaturated groups bonded to silicon, especially in the presence of a platinum catalyst; or by dehydrogenation crosslinking condensation reaction between a diorganopolysiloxane containing hydroxyl end groups and a diorganopolysiloxane containing at least one hydrogen bonded to silicon, especially in the presence of an organotin; or by crosslinking condensation reaction of a diorganopolysiloxane containing hydroxyl end groups and of a hydrolysable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, especially in the presence (C) of a platinum catalyst, as described, for instance, in patent application EP-A-295 886.

In particular, the organopolysiloxane elastomer may be obtained by reaction of a dimethylpolysiloxane containing dimethylvinylsiloxy end groups and of methylhydrogenpolysiloxane containing trimethylsiloxy end groups, in the presence of a platinum catalyst.

Compound (A) is the base reagent for the formation of organopolysiloxane elastomer, and the crosslinking is performed by addition reaction of compound (A) with compound (B) in the presence of the catalyst (C).

Compound (A) is in particular an organopolysiloxane containing at least two hydrogen atoms bonded to different silicon atoms in each molecule.

Compound (A) may have any molecular structure, especially a linear-chain or branched-chain structure or a cyclic structure.

Compound (A) may have a viscosity at 25° C. ranging from 1 to 50 000 centistokes, especially so as to be miscible with compound (B).

The organic groups bonded to the silicon atoms of compound (A) may be alkyl groups such as methyl, ethyl, propyl, butyl, octyl; substituted alkyl groups such as 2-phenylethyl, 2-phenylpropyl or 3,3,3-trifluoropropyl; aryl groups such as phenyl, tolyl, xylyl; substituted aryl groups such as phenylethyl; and substituted monovalent hydrocarbon-based groups such as an epoxy group, a carboxylate ester group or a mercapto group.

Compound (A) may thus be chosen from methylhydrogenpolysiloxanes containing trimethylsiloxy end groups, dimethylsiloxane-methylhydrosiloxane copolymers containing trimethylsiloxy end groups, and dimethylsiloxane-methylhydrosiloxane cyclic copolymers.

Compound (B) is advantageously a diorganopolysiloxane containing at least two lower alkenyl groups (for example $C_2$-$C_4$); the lower alkenyl group may be chosen from vinyl, allyl and propenyl groups. These lower alkenyl groups may be located in any position of the organopolysiloxane molecule, but are preferably located at the ends of the organopolysiloxane molecule. The organopolysiloxane (B) may have a branched-chain, linear-chain, cyclic or network structure, but the linear-chain structure is preferred. Compound (B) may have a viscosity ranging from the liquid state to the gum state. Preferably, compound (B) has a viscosity of at least 100 centistokes at 25° C.

Besides the abovementioned alkenyl groups, the other organic groups bonded to the silicon atoms in compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The organopolysiloxanes (B) may be chosen from methylvinylpolysiloxanes, methylvinylsiloxane-dimethylsiloxane copolymers, dimethylpolysiloxanes containing dimethylvinylsiloxy end groups, dimethylsiloxane-methylphenylsiloxane copolymers containing dimethylvinylsiloxy end groups, dimethylsiloxane-diphenylsiloxane-methylvinylsiloxane copolymers containing dimethylvinylsiloxy end groups, dimethylsiloxane-methylvinylsiloxane copolymers containing trimethylsiloxy end groups, dimethylsiloxane-methylphenylsiloxane-methylvinylsiloxane copolymers containing trimethylsiloxy end groups, methyl(3,3,3-trifluoropropyl)polysiloxanes containing dimethylvinylsiloxy end groups, and dimethylsiloxane-methyl(3,3,3-trifluoropropyl)siloxane copolymers containing dimethylvinylsiloxy end groups.

In particular, the organopolysiloxane elastomer may be obtained by reaction of dimethylpolysiloxane containing dimethylvinylsiloxy end groups and of methylhydrogenpolysiloxane containing trimethylsiloxy end groups, in the presence of a platinum catalyst.

Advantageously, the sum of the number of ethylenic groups per molecule in compound (B) and of the number of hydrogen atoms bonded to silicon atoms per molecule in compound (A) is at least 5.

It is advantageous for compound (A) to be added in an amount such that the molecular ratio between the total amount of hydrogen atoms bonded to silicon atoms in compound (A) and the total amount of all the ethylenically unsaturated groups in compound (B) is within the range of from 1.5/1 to 20/1.

Compound (C) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C) is preferably added in an amount of from 0.1 to 1000 parts by weight and better still from 1 to 100 parts by weight, as clean platinum metal, per 1000 parts by weight of the total amount of compounds (A) and (B).

The elastomer is advantageously a non-emulsifying elastomer.

The term "non-emulsifying" defines organopolysiloxane elastomers not containing any hydrophilic chains, and in particular not containing any polyoxyalkylene units (especially polyoxyethylene or polyoxypropylene) or any polyglyceryl units. Thus, according to one particular embodiment of the invention, the composition comprises an organopolysiloxane elastomer that is free of polyoxyalkylene units and polyglyceryl units.

Non-emulsifying elastomers are especially described in patents EP 242 219, EP 285 886 and EP 765 656 and in patent application JP-A-61-194 009.

Non-emulsifying elastomers that may be used more particularly include those sold under the names KSG-6, KSG-15, KSG-16, KSG-18, KSG-41, KSG-42, KSG-43 and KSG-44 by the company Shin-Etsu, DC 9040 and DC 9041 by the company Dow Corning, and SFE 839 by the company General Electric.

Spherical non-emulsifying elastomers that may be used include those sold under the names DC 9040, DC 9041, DC 9509, DC 9505 and DC 9506 by the company Dow Corning.

In an embodiment, the organopolysiloxane elastomer particles are conveyed in the form of a gel formed from an elastomeric organopolysiloxane included in at least one hydrocarbon-based oil and/or one silicone oil. In these gels, the organopolysiloxane particles are often non-spherical particles.

As preferred non-emulsifying silicone elastomer in gel form, we may cite the INCI Name products Dimethicone crosspolymers such as DC9041, DC9045 from Dow Corning.

In another embodiment, the organopolysiloxane elastomer particles are conveyed in the form of a powder.

As preferred non-emulsifying silicone elastomer in powder form, we may cite the INCI Name products Dimethicone/Vinyldimethicone crosspolymer such as the DC9506 and DC9701 from Dow Corning and KSG6 from Shin Etsu.

In another embodiment, the composition of the invention comprises at least one silicone elastomer powder coated with a silicone resin. The silicone elastomer powder is spherical and may be obtained especially via the processes for synthesizing non-emulsifying elastomers described above. The silicone elastomer powder is coated with silicone resin.

According to one preferred embodiment, the silicone resin may be a silsesquioxane resin, as described, for example, in U.S. Pat. No. 5,538,793, the content of which is incorporated herein by way of reference. Such elastomer powders coated with silicone resin are especially sold under the names KSP-100, KSP-101, KSP-102, KSP-103, KSP-104 and KSP-105 by the company Shin-Etsu. Such powders correspond to the INCI name dimethicone silsesquioxane crosspolymer, and in particular vinyl dimethicone/methicone silsesquioxane crosspolymer. As a preferred elastomer powder coated with silicone resin, we may use KSP 100.

The silicone elastomer particles may have a JIS-A hardness of less than or equal to 80 (especially ranging from 5 to 80) and preferably less than or equal to 65 (especially ranging from 5 to 65).

The JIS-A hardness is measured according to the method JIS K 6301 (1995) established by the Japanese Industrial Standards Committee.

In particular, the silicone elastomer particles may have a mean size ranging from 0.1 to 500 preferably from 3 to 200 µm and better still from 10 to 20 µm. These particles may be of spherical, flat or amorphous shape, and preferably of spherical shape.

This organopolysiloxane elastomer or silicon elastomer is present in the cosmetic composition according to the present invention generally in a content ranging from 0.1% to 20% by weight of active material (=dry matter) and preferably from 0.5% to 15% by weight, and more preferably 0.5% to 10% by weight, relative to the total weight of said composition.

[Oil Absorbing Agent with Oil Absorption Capability of 1 ml/1 g or More]

The cosmetic composition according to the present invention comprises at least one oil absorbing agent with oil absorption capability of 1 ml/1 g or more in an amount of more than 1% by weight relative to the total weight of composition. The above agent has capacity for absorbing and/or adsorbing an oil or a liquid fatty substance, for instance sebum (from the skin).

This oil-absorbing agent, preferably oil-absorbing filler, may also advantageously have a BET specific surface area of greater than or equal to 300 $m^2/g$, preferably greater than 500 $m^2/g$ and preferentially greater than 600 $m^2/g$, and especially less than 1500 $m^2/g$.

The BET specific surface area is determined according to the BET (Brunauer-Emmet-Teller) method described in the Journal of the American Chemical Society, vol. 60, page 309, February 1938 and corresponding to the international standard ISO 5794/1 (appendix D). The BET specific surface area corresponds to the total specific surface area (thus including micropores) of the powder.

The oil-absorbing agent under consideration according to the invention is thus characterized in that it has an oil uptake of greater than or equal to 1 ml/g, preferably greater than or equal 1.5 ml/g, especially ranging from 1.5 ml/g to 20 ml/g, or even ranging from 1.5 ml/g to 15 ml/g. It preferably has an oil uptake of greater than or equal to 2 ml/g, especially ranging from 2 ml/g to 20 ml/g, or even ranging from 2 ml/g to 15 ml/g.

This oil uptake, which corresponds to the amount of oil absorbed and/or adsorbed by the oil-absorbing agent, may be characterized by measuring the wet point according to the method described below. The oil-absorbing capacity measured at the wet point, noted Wp, corresponds to the amount of oil that needs to be added to 100 g of particle in order to obtain a homogeneous paste.

The oil uptake of an oil-absorbing agent can be measured according to the method for determining the oil uptake of a powder described in standard NF T 30-022. It corresponds to the amount of oil adsorbed onto the available surface of the powder, by measuring the wet point.

An amount m (in grams) of the oil-absorbing agent of between about 0.5 g and 5 g (the amount depends on the density of the oil-absorbing agent, but typically 2 g) is placed on a glass plate and isononyl isononanoate is then added dropwise.

After addition of 4 to 5 drops of isononyl isononanoate, the isononyl isononanoate is incorporated into the oil-absorbing agent using a spatula, and addition of the isononyl isononanoate is continued until a conglomerate of isononyl isononanoate and powder has formed. At this point, the isononyl isononanoate is added one drop at a time and the mixture is then triturated with the spatula. The addition of isononyl isononanoate is stopped when a firm, smooth paste is obtained. This paste must be able to be spread on the glass plate without cracking or forming lumps. The volume Vs (expressed in ml) of isononyl isononanoate used is then noted.

The oil uptake corresponds to the ratio Vs/m.

The oil-absorbing agent under consideration according to the invention may be of organic or inorganic nature.

The oil-absorbing agent having oil absorption capacity greater than or equal to 1 ml/g may be chosen more particularly from silicas, polyamide (in particular Nylon-6) powders, powders of acrylic polymers, especially of polymethyl methacrylate, of polymethyl methacrylate/ethylene glycol dimethacrylate, of polyallyl methacrylate/ethylene glycol dimethacrylate or of ethylene glycol dimethacrylate/lauryl methacrylate copolymer; perlites; magnesium carbonate, and mixtures thereof. It is preferable that the oil-absorbing agent be selected from powders of acrylic polymers, especially of polymethylmethacrylate.

A person skilled in the art will select, among the above-mentioned materials, fillers with an oil uptake of greater than or equal to 1 ml/g, preferably greater than or equal to 1.5 ml/g and preferably greater than or equal to 2 ml/g, which are in this respect suitable for use in the invention.

Advantageously, the oil-absorbing agent may be a powder uncoated or coated with a hydrophobic treatment agent.

The hydrophobic treatment agent may be chosen especially from fatty acids such as stearic acid; metal soaps such as aluminium dimyristate, the aluminium salt of hydrogenated tallow glutamate; amino acids; N-acylamino acids or salts thereof; lecithin, isopropyl triisostearyl titanate, mineral waxes, and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be aluminium, magnesium, calcium, zirconium, zinc, sodium or potassium salts. The amino acid may be, for example, lysine, glutamic acid or alanine.

The term "alkyl" mentioned in the compounds mentioned previously especially denotes an alkyl group containing from 1 to 30 carbon atoms and preferably containing from 5 to 16 carbon atoms.

Examples of the oil-absorbing agents in accordance with the present invention include fillers with an oil uptake of greater than or equal to 1 ml/g, preferably greater than or equal to 1.5 ml/g, described below, with their oil uptake value measured according to the protocol described previously.

Silica powders that may be mentioned include:
porous silica microspheres, especially those sold under the names Sunsphere® H53 and Sunsphere® H33 (oil uptake equal to 3.70 ml/g) by the company Asahi Glass; MSS-500-3H by the company Kobo;
polydimethylsiloxane-coated amorphous silica microspheres, especially those sold under the name SA Sunsphere® H33 (oil uptake equal to 2.43 ml/g),
amorphous hollow silica particles, especially those sold under the name Silica Shells by the company Kobo (oil uptake equal to 5.50 ml/g), and
precipitated silica powders surface-treated with a mineral wax, such as precipitated silica treated with a polyethylene wax, and especially those sold under the name Acematt OR 412 by the company Evonik-Degussa (oil uptake equal to 3.98 ml/g).

Acrylic polymer powders that may be mentioned include:
porous polymethyl methacrylate (INCI name methyl methacrylate crosspolymer) such as the spheres sold under the name Covabead LH85 by the company Sensient,
porous polymethyl methacrylate/ethylene glycol dimethacrylate spheres sold under the name Microsponge 5640 by the company Cardinal Health Technologies (oil uptake equal to 1.55 ml/g), and
ethylene glycol dimethacrylate/lauryl methacrylate copolymer powders, especially those sold under the name Polytrap® 6603 from the company Dow Corning (oil uptake equal to 6.56 ml/g).

Polyamide powders that may be mentioned include:
nylon-6 powder, especially the product sold under the name Pomp610 by the company UBE Industries (oil uptake equal to 2.02 ml/g).

A perlite powder that may especially be mentioned is the product sold under the name Optimat 14300R by the company World Minerals (oil uptake equal to 2.4 ml/g).

A magnesium carbonate powder that may especially be mentioned is the product sold under the name Tipo Carbomagel by the company Buschle & Lepper (oil uptake equal to 2.14 ml/g).

The oil-absorbing fillers that are particularly preferred are silica powders and more particularly the products sold under the name Sunsphere® H33 by the company Asahi Glass; nylon-6 powder and porous polymethyl methacrylate (INCI name methyl methacrylate crosspolymer) such as the spheres sold under the name Covabead LH85 by the company Sensient.

The oil-absorbing agents(s) with an oil uptake of greater than or equal to 1 ml/g, preferably greater or equal than 1.5 ml/g may be present in a cosmetic composition according to the present invention in a content ranging from 1% to 50% by weight, preferably ranging from 1% to 40% by weight and preferentially ranging from 2% to 20% by weight relative to the total weight of the composition.

[Optional Components]

The cosmetic composition according to the present invention may further comprise at least one additional filler and/or at least one oil.

As used herein, the term "filler" should be understood as meaning colorless natural or synthetic particles of any shape which are insoluble in the medium of the composition, whatever the temperature at which the composition is manufactured. Thus, the filler is different from the coloring pigment as described above.

The fillers may be inorganic or organic and of any shape (for instance, platelet, spherical, and oblong shapes) and with any crystallographic form (for example, sheet, cubic, hexagonal, orthorhombic, and the like). Examples of suitable additional fillers include, but are not limited to, talc; mica; silica; kaolin; powders of polyamide such as Nylon®; poly-β-3-alanine powders; polyethylene powders; polyurethane powders, such as the powder formed of hexamethylene diisocyanate and trimethylol hexyllactone copolymer sold under the name Plastic Powder D-400 by Toshiki; the powders formed of tetrafluoroethylene polymers (Teflon®); lauroyllysine; starch; boron nitride; polymeric hollow microspheres, such as microspheres of poly(vinylidene chloride)/acrylonitrile, for example Expancel® (Nobel Industrie), and microspheres of acrylic acid copolymers; silicone resin powders, for example, silsesquioxane powders (for instance, silicone resin powders disclosed in European Patent No. 0 293 795 and Tospearls® from Toshiba); poly (methyl methacrylate) particles; precipitated calcium carbonate; magnesium carbonate; basic magnesium carbonate; hydroxyapatite; hollow silica microspheres; glass microcapsules; ceramic microcapsules; metal soaps derived from organic carboxylic acids comprising from 8 to 22 carbon atoms, for example, from 12 to 18 carbon atoms, such as zinc stearate, magnesium stearate, lithium stearate, zinc laurate, and magnesium myristate; barium sulphate; and mixtures thereof.

The filler may be present in the composition in an amount ranging from 0.1% to 80% by weight, with respect to the total weight of the composition, for example, from 1% to 25% by weight, or from 3% to 15% by weight.

The term "oil" is understood to mean a fatty substance which is liquid at ambient temperature (25° C.).

Use may be made, as oils which can be used in the composition of the invention, for example, of hydrocarbon oils of animal origin, such as perhydrosqualene (or squalane); hydrocarbon oils of vegetable origin, such as triglycerides of caprylic/capric acids, for example those marketed by Stearineries Dubois or those marketed under the trademarks Miglyol 810, 812 and 818 by Dynamit Nobel, or oils of vegetable origin, for example sunflower, maize, soybean, cucumber, grape seed, sesame, hazelnut, apricot, macadamia, arara, coriander, castor, avocado or jojoba oil or shea butter oil; synthetic oils; silicone oils, such as volatile or non-volatile polymethylsiloxanes (PDMSs) comprising a linear or cyclic silicone chain which are liquid or paste at ambient temperature; fluorinated oils, such as those which are partially hydrocarbon and/or silicone, for example those described in JP-A-2-295912; ethers, such as dicaprylyl ether (CTFA name); and esters, such as benzoate $C_{12}$-$C_{15}$ fatty alcohols (Finsolv TN from Finetex); arylalkyl benzoate derivatives, such as 2-phenylethyl benzoate (X-Tend 226 from ISP); amidated oils, such as isopropyl N-lauroylsarcosinate (Eldew SL-205 from Ajinomoto), and their mixtures.

The oily phase can also comprise one or more fatty substances selected, for example, from fatty alcohols (cetyl alcohol, stearyl alcohol, cetearyl alcohol), fatty acids (stearic acid) or waxes (paraffin wax, polyethylene waxes, carnauba wax, beeswax). The oily phase can comprise lipophilic gelling agents, surfactants or also organic or inorganic particles.

The oily phase can preferably represent from 1 to 70% of oil by weight, with respect to the total weight of the composition.

The composition according to the present invention may further comprise at least one additional conventional cosmetic ingredient which may be chosen, for example, from hydrophilic or lipophilic gelling and/or thickening agents, surfactants, antioxidants, fragrances, preservatives, neutralizing agents, sunscreens, vitamins, moisturizing agents, self-tanning compounds, antiwrinkle active agents, emollients, hydrophilic or lipophilic active agents, agents for combating pollution and/or free radicals, sequestering agents, film-forming agents, dermo-decontracting active agents, soothing agents, agents which stimulate the synthesis of dermal or epidermal macromolecules and/or which prevent their decomposition, antiglycation agents, agents which combat irritation, desquamating agents, depigmenting agents, antipigmenting agents, propigmenting agents, NO-synthase inhibitors, agents which stimulate the proliferation of fibroblasts and/or keratinocytes and/or the differentiation of keratinocytes, agents which act on microcirculation, agents which act on energy metabolism of the cells, healing agents, and mixtures thereof.

In a particular embodiment, the cosmetic composition of the present invention comprises a low amount of additional coloring pigments. As the additional coloring pigments, mention may be made of those to be used as the coloring pigments which may be present in the coating layer of the small or large particle.

The cosmetic composition according to the present invention may comprise from 0 to 5% of additional coloring pigments relative to the total weight of the composition.

In a particular embodiment, the cosmetic composition according to the present invention comprises from 0 to 3% of additional coloring pigments relative to the total weight of the composition.

The composition according to the present invention may be in various forms, for example, suspensions, dispersions, solutions, gels, emulsions, such as oil-in-water (O/W), water-in-oil (W/O), and multiple (e.g., W/O/W, polyol/O/W, and O/W/O) emulsions, creams, foams, sticks, dispersions of vesicles, for instance, of ionic and/or nonionic lipids, two-phase and multi-phase lotions, sprays, powders, and pastes. The composition may be anhydrous, for example, it can be an anhydrous paste or stick. The composition may also be a leave-in composition.

According to one embodiment, the cosmetic composition according to the present invention may be in the form of a powdery composition or a liquid or solid composition, such as an oily-solid cosmetic composition or an anhydrous composition.

In particular, the powdery cosmetic composition according to the present invention can have reduced friction which provides a smooth feeling to use, and can have good compactability which provides high stability against physical impact, due to the inclusion of the composite pigment according to the present invention.

Furthermore, the powdery cosmetic composition according to the present invention can show preferable cosmetic effects such as good fitting to the skin, homogeneous appearance, hiding the color of the skin, hiding the pores and lines on the skin, making the pores and lines on the skin less remarkable, and matt appearance, due to the inclusion of the combination of the above composite pigment, the organopolysiloxane elastomer and the specific oil absorbing agent with a specific amount, according to the present invention.

On the other hand, the liquid cosmetic composition according to the present invention can also show good skin pore hiding effects and good visual optical effects such as matt and haze effects, due to the inclusion of the combination of the above composite pigment, the organopolysiloxane elastomer and the specific oil absorbing agent with a specific amount, according to the present invention.

In particular, the powdery and liquid cosmetic composition according to the present invention has better UV filtering effects, and optionally better coloring effects, in addition to reduce the risk of fine particles of inorganic solid UV filter(s) and optional coloring pigment(s) penetrating into the skin via pores on the skin.

According to another embodiment, the cosmetic composition according to the present invention may be in the form of, for example, a compact powder, a lotion, a serum, a milk, a cream, a base foundation, an undercoat, a make-up base coat, a foundation, a face powder, cheek rouge, a lipstick, a lip cream, an eye shadow, an eyeliner, a loose powder, a concealer, a nail coat, mascara, a sunscreen and the like.

According to another embodiment, the cosmetic composition according to the present invention may be in the form of a foam.

According to this embodiment, the cosmetic composition according to the present invention can be packaged in a foam dispenser. It can involve either products referred to as "aerosols" dispensed from a pressurized container by means of a propellant gas and thus forming a foam at the time of their dispensing, or products dispensed from a container by means of a mechanical pump connected to a dispensing head where the passage of the cosmetic composition through the dispensing head transforms it into a foam in the area of the outlet orifice of such a head at the latest.

According to a first variant, the dispenser can be an aerosol furthermore containing the cosmetic composition according to the present invention; and a propellant gas. For the purposes of the invention, the term "propellant" means any compound that is gaseous at a temperature of 20° C. and at atmospheric pressure, and that can be stored under pressure in liquid or gaseous form in an aerosol container. The propellant may be chosen from optionally halogenated volatile hydrocarbons, such as n-butane, propane, isobutane, pentane or a halogenated hydrocarbon, and mixtures thereof. Carbon dioxide, nitrous oxide, dimethyl ether (DME), nitrogen or compressed air may also be used as propellant. Mixtures of propellants may also be used. Dimethyl ether and/or non-halogenated volatile hydrocarbons are preferably used.

The propellant gas which can be used may be chosen among the previously mentioned gases and in particular among carbon dioxide, nitrogen, nitrogen oxide, dimethyl ether, volatile hydrocarbons such as butane, isobutane, propane and pentane, and mixtures thereof.

According to another variant, the cosmetic composition according to the present invention can be in a "pump bottle" type foam dispenser. These dispensers include a dispensing head for delivering the cosmetic composition, a pump and a plunger tube for transferring the cosmetic composition from the container, into the head, for dispensing the product. The foam is formed by forcing the cosmetic composition to pass through a material including a porous substance such as a sintered material, a filtering grid of plastic or metal, or similar structures.

Such dispensers are known to a person skilled in the art and are described in the U.S. Pat. No. 3,709,437 (Wright), U.S. Pat. No. 3,937,364 (Wright), U.S. Pat. No. 4,022,351 (Wright), U.S. Pat. No. 4,1147,306 (Bennett), U.S. Pat. No. 4,184,615 (Wright), U.S. Pat. No. 4,598,862 (Rice), U.S. Pat. No. 4,615,467 (Grogan et al.), and U.S. Pat. No. 5,364,031 (Tamiguchi et al.).

[Cosmetic Process]

Another aspect of the present invention is a cosmetic process using the cosmetic composition according to the present invention as explained above.

The cosmetic process according to the present invention includes at least a step of applying the cosmetic composition according to the present invention onto the skin.

The cosmetic process according to the present invention can improve UV filtration and/or pore hiding on the skin, for a long period of time such as all day long, without deteriorating other cosmetic effects such as skin brightening, color homogeneity and smoothening effects.

It is to be understood that a person skilled in the art can choose the appropriate presentation form, as well as its method of preparation, on the basis of his/her general knowledge, taking into account the nature of the constituents used, for example, their solubility in the vehicle, and the application envisaged for the composition.

EXAMPLES

The present invention will be described in more detail by way of examples, which however should not be construed as limiting the scope of the present invention.

Pigment Examples

The components shown in Table 1 were subjected to a hybridizer process using a Hybridizer equipped with a high speed rotor having a plurality of blades in a chamber in dry conditions, marketed by Nara Machinery Co., Ltd. in Japan to obtain a composite pigment.

In detail, for each of Pigment Examples 1 to 4, the components shown in Table 1 were mixed at the mixing ratio (the numerals in Table 1 are based on parts by weight) shown in Table 1 in a plastic bag by hand shaking for a short period of time. The mixture was put in the Hybridizer, and the rotor was revolved at 8,000 rpm (100 m/s linear velocity) for 3 minutes to obtain the composite pigments according to Pigment Examples 1 to 4.

As Control, a marketed composite pigment with silica and titanium dioxide (SUNSIL-T$^m$50 marketed by Sunjin Chemical Co., Ltd.) was used. In this composite pigment, titanium oxide fine particles are distributed in a solid silica particle. The particle size of the composite pigment according to Control was 4 µm.

(UV Absorbance Evaluation)

Absorbance of UV waves of each of the composite pigments according to Pigment Examples 1 to 4 and Control was measured by use of a UV/VIS spectrophotometer type V-550 (JASCO, Japan) as follows.

A solvent was prepared by mixing isododecane and polyhydroxystearic acid such that the concentration of polyhydroxystearic acid was 3 wt %.

Each of the composite pigments according to Pigment Examples 1 to 4 and Control was dispersed in the above solvent by using ultrasonic waves for 1 minute to obtain a sample, such that the concentration of the composite pigment in the sample was 0.1 wt %. If agglomerates were still present, the ultrasonic treatment was repeated.

The obtained sample was put into a quartz cell having a 2 mm light pathway. The UV absorbance of the sample in the wavelength of from 280 to 400 nm was measured by use of a UV/VIS spectrophotometer type V-550 (JASCO, Japan).

The results are shown in Table 1 in the column of "UV*".

It is clear that the UV absorbance of the composite pigments according to Pigment Examples 1 to 4 is enhanced.

Since a relatively large amount of $TiO_2$ is used in Pigment Examples 1 and 3, the UV absorbance value of Examples 1 and 3 is higher than that of Examples 2 and 4, respectively. Since $TiO_2$ nano particles easily form aggregations which are difficult to show good UV absorption, it is surprising to observe that a relatively large amount of $TiO_2$ can exert higher UV absorbance for the composite pigment according to Examples 1 and 3.

TABLE 1

| | Small Hollow Core Styrene/Acrylate | Small Solid Core | Large Core | | UV filter | |
| --- | --- | --- | --- | --- | --- | --- |
| | Copolymer | PMMA(1) | PMMA(2) | Nylon 12 | $TiO_2$ | |
| | Particle Size | | | | | |
| | 350 nm | 350 nm | 6 µm | 5 µm | 15 nm | UV* |
| Pigment Ex. 1 | 35 | — | 15 | — | 50 | 129 |
| Pigment Ex. 2 | 50 | — | 20 | — | 30 | 102 |
| Pigment Ex. 3 | — | 35 | — | 15 | 50 | 148 |
| Pigment Ex. 4 | — | 35 | — | 35 | 30 | 72 |
| Control | — | — | — | — | — | 19 |

Syrene/Acrylate Copolymer: Sunspheres marketed by Rohm and Haas
PMMA(1): MP-2200 marketed by Soken in Japan
PMMA(2): MR-7GC marketed by Soken in Japan
Nylon 12: SP-500 marketed by Toray in Japan
$TiO_2$: MT-100 TV marketed by Tayca in Japan
UV*: UV absorbance in the wavelength region from 280 to 400 nm Example 1 and Comparative Examples 1 to 4

A make-up base in the form of a W/O emulsion was prepared by mixing the components shown in Table 2. Unless otherwise mentioned, the values in Table 2 are expressed as % by weight relative to the total weight of the composition.

TABLE 2

| Phase | Component | Ex. 1 | Comp. Ex. 1 | Comp. Ex. 2 | Comp. Ex. 3 | Comp. Ex. 4 |
|---|---|---|---|---|---|---|
| A | Cyclopentasiloxane | 21.50 | 21.50 | 21.50 | 28.77 | 25.78 |
|   | Dimethicone | — | 8.30 | — | — | — |
|   | BIS-PEG/PPG-14/14 Dimethicone/Cyclopentasiloxane | 1.00 | 1.00 | 1.00 | 1.00 | 1.00 |
|   | PEG-10 Dimethicone | 2.00 | 2.00 | 2.00 | 2.00 | 2.00 |
|   | Dimethicone/Dimethicone Crosspolymer (DC9041 from Dow Corning) | 8.30 | — | 8.30 | 8.30 | 8.30 |
|   | Tribehenin | 1.00 | 1.00 | 1.00 | 1.00 | 1.00 |
|   | Ethylhexylmethoxycinnamate | 2.50 | 2.50 | 2.50 | 2.50 | 2.50 |
| B | Iron oxide | 0.07 | 0.07 | 0.07 | 0.07 | 0.07 |
|   | Titanium oxide | 0.93 | 0.93 | 0.93 | 0.93 | 0.93 |
| C | Pigment Example 4 | 10 | 10 | — | — | — |
|   | Nylon-12 | — | — | 3.50 | — | — |
|   | PMMA | — | — | 3.50 | — | — |
|   | $TiO_2$ | — | — | 3.00 | — | — |
|   | Titanium oxide* | — | — | — | 2.73 | — |
|   | Silica/$TiO_2$ | — | — | — | — | 5.72 |
| D | HDI/Trimethylolhexyllactone Crosspolymer | 4.00 | 4.00 | 4.00 | 4.00 | 4.00 |
|   | Talc | 1.00 | 1.00 | 1.00 | 1.00 | 1.00 |
| E | Magnesium sulfate | 0.70 | 0.70 | 0.70 | 0.70 | 0.70 |
|   | Phenoxyethanol | 0.50 | 0.50 | 0.50 | 0.50 | 0.50 |
|   | Caprylyl glycol | 0.50 | 0.50 | 0.50 | 0.50 | 0.50 |
|   | Maltitol/Sorbitol | 1.00 | 1.00 | 1.00 | 1.00 | 1.00 |
|   | Butyleneglycol | 3.50 | 3.50 | 3.50 | 3.50 | 3.50 |
|   | Glycerin | 2.50 | 2.50 | 2.50 | 2.50 | 2.50 |
|   | Alcohol | 1.00 | 1.00 | 1.00 | 1.00 | 1.00 |
|   | Water | 38.00 | 38.00 | 38.00 | 38.00 | 38.00 |

Nylon 12: SP-500 marketed by Toray in Japan
PMMA: MP-2200 marketed by Soken in Japan
$TiO_2$: MT-100 TV marketed by Tayca in Japan
Titanium oxide*: MT-700Z marketed by Tayca in Japan
Silica/$TiO_2$: SUNSIL-T™50 marketed by Sunjin Chemical Co., Ltd. in Japan The components in Phase A were mixed together in a container with a magnetic stirrer at a temperature of from 60 to 80° C. Then, the components in Phases B, C and D were added to the mixture, and stirred. Next, the components in Phase E were added to the mixture, and stirred.

Lastly, the mixture obtained was homogenized to obtain the make-up bases according to Example 1 and Comparative Examples 1 to 4.

In Comparative Example 1, the silicone elastomer (Dimethicone/Dimethicone Crosspolymer) was replaced with dimethicone.

In Comparative Example 2, the composite pigment according to Pigment Example 2 was replaced with a simple mixture of the raw materials (Nylon-12, PMMA and $TiO_2$ nanoparticles) of the composite pigment according to Pigment Example 2.

In Comparative Example 3, the composite pigment according to Pigment Example 2 was replaced with a conventional $TiO_2$ product.

In Comparative Example 4, the composite pigment according to Pigment Example 2 was replaced with the composite pigment according to Control.

(In Vitro SPF Value Evaluation)

The make-up base was applied onto a PMMA plate in an amount of 1 mg/cm², and the SPF value of the make-up base sample was measured by an SPF analyzer UV-2000S. The results are shown in Table 3 and FIG. 1.

As shown in Table 3 and FIG. 1, the composition according to Example 1 showed a significantly higher UV filtration than those of the compositions according to Comparative Examples 2 to 4. These results confirm that the use of organopolysiloxane elastomer and composite pigment improve the UV filtering effect of a cosmetic composition.

(Sensory Evaluation)

Each of the make-up bases according to Example 1 and Comparative Examples 1 to 4, in an amount of 0.1 g, was applied to the skin of 6 panelists, and the cosmetic effects (i.e., pore hiding effect, skin brightening effect, color homogeneity, and smoothening effect) of each make-up base were evaluated by experts and compared.

Specifically, the make-up base according to Example 1 was applied to half of the face, and the make-up base according to any of the make-up bases according to Comparative Examples 1 to 4 was applied to the other half of the face. The cosmetic effects of the former were compared to those of the latter. The evaluations by 6 panelists were averaged. The results are shown in Table 3.

TABLE 3

|   | Ex. 1 | Comp. Ex. 1 | Comp. Ex. 2 | Comp. Ex. 3 | Comp. Ex. 4 |
|---|---|---|---|---|---|
| Pore Hiding | Good | Bad | Good | Good | Good |
| Skin Brightening | Very good | Good | Good | Very good | Fair |
| Color Homogeneity | Very good | Fair | Good | Bad | Fair |
| Smoothening | Good | Fair | Fair | Bad | Fair |
| In-vitro SPF | 15.0 | N.A. | 10.3 | 5.3 | 3.3 |

As compared to Comparative Example 2, Example 1 and Comparative Examples 2 to 4 showed significantly stronger pore hiding effect once applied onto the skin. The composition according to Example 1 showed better cosmetic effects in terms of not only pore hiding but also skin brightening, color homogeneity and smoothening, than the composition according to any of Comparative Examples 2 to 4.

The above results demonstrate that the composition according to Example 1 based on a combination of the composite pigment and the silicon elastomer can provide simultaneously good UV filtration effects and skin pore hiding effects, as well as other cosmetic effects such as skin brightening, color homogeneity and smoothening effects.

Example 2 and Comparative Example 5

A make-up base in the form of a W/O emulsion was prepared by mixing the components shown in Table 4. Unless otherwise mentioned, the values in Table 4 are expressed as % by weight relative to the total weight of the composition.

TABLE 4

| Phase | Component | Ex. 2 | Comp. Ex. 5 |
|---|---|---|---|
| A | Dimethicone | 8.70 | 10.70 |
|   | Cetyl-PEG/PPG-10/1 Dimethicone | 1.00 | 1.00 |
|   | PEG-10 Dimethicone | 2.00 | 2.00 |
|   | Dimethicone/Dimethicone Crosspolymer (DC9041 from Dow Corning) | 8.30 | 8.30 |
|   | Mixture of n-undecane: n-tridecane, (majority of n-undecane) as prepared in WO2008/155059 | 12.00 | 12.00 |
|   | Tribehenin | 1.00 | 1.00 |
|   | Drometrizole trisiloxane | 3.00 | 3.00 |
| B | Iron oxide | 0.14 | 0.14 |
|   | Titanium oxide | 0.86 | 0.86 |
| C | Pigment Example 1 | 8.00 | 8.00 |
|   | Vinyl dimethicone/Methicone silsesquioxane | 4.00 | 4.00 |
|   | Methy methacrylate crosspolymer** | 4.00 | — |
|   | Polymethyl methacrylate*** | — | 4.00 |
| D | Magnesium Sulfate | 0.70 | 0.70 |
|   | Phenoxyethanol | 0.50 | 0.50 |
|   | Maltitol/Sorbitol | 1.00 | 1.00 |
|   | Caprylyl glycol | 0.50 | 0.50 |
|   | Butyleneglycol | 2.00 | 2.00 |
|   | Glycerin | 3.00 | 3.00 |
|   | Water | 21.00 | 21.00 |
|   | Alcohol | 4.00 | 4.00 |
| E | Terephthalylidene Dicamphor Sulphonic Acid | 12.00 | 12.00 |
|   | Triethanolamine | 2.30 | 2.30 |

Methy methacrylate crosspolymer**: Covabead LH85 marketed by Wacker
Polymethyl methacrylate***: Micropearl M100 marketed by Seppic The oil absorption capacities of the porous PMMA (Methy methacrylate crosspolymer) and the non-porous PMMA (Polymethyl methacrylate) in Table 4 were about 120 ml/100 g and 50 ml/100 g, respectively.

Example 2' according to the present invention was also made, wherein Pigment Example 1 was replaced by Pigment Example 2.

(Sensory Evaluation)

Each of the make-up bases according to Example 2 and Comparative Example 5, in an amount of 0.1 g, was applied to the skin of 6 panelists, and the pore hiding effect of each make-up base was evaluated by experts and compared.

Specifically, the make-up base according to Example 2 was applied to half of the face, and the make-up base according to Comparative Example 5 was applied to the other half of the face. The pore hiding effect of the former was compared to those of the latter. The evaluations by 6 panelists were averaged.

The composition according to Example 2 showed pore hiding effect for a longer period of time than the composition according to Comparative Example 5.

The above results demonstrate that the composition according to Example 2 based on a combination of the composite pigment, the silicon elastomer and the absorbing agent with oil absorption capability of 1 ml/1 g or more can provide simultaneously good UV filtration effects and skin pore hiding effects which can last for a long period of time.

Similar results were obtained with the Example 2'.

The invention claimed is:

1. A cosmetic composition comprising:
   (i) at least one composite pigment comprising:
      (a) at least one small particle comprising a styrene/acrylate copolymer, wherein the at least one small particle is at least partially covered with at least one coating layer comprising at least one particulate titanium dioxide,
      (b) at least one large particle comprising a polymethyl methacrylate polymer, and
      (c) optionally at least one coloring pigment,
         wherein the at least one small particle has a mean particle size ranging from about 100 nm to about 600 nm,
         wherein the at least one large particle has a mean particle size of greater than about 2 μm,
         wherein the weight ratio of the at least one small particles to the at least one large particle ranges from 50:50 to 90:10, and
         wherein the composite pigment is obtained by a mechanochemical fusion process;
   (ii) at least one non-emulsifying organopolysiloxane elastomer chosen from dimethicone crosspolymers, present in an amount ranging from about 8.3% to about 10% by weight relative to the total weight of the composition; and
   (iii) at least one porous oil absorbing agent with an oil absorption capability of from 1 to 15 mL/g,
      wherein the at least one porous oil absorbing agent is present in an amount greater than about 1% by weight, relative to the total weight of composition.

2. The cosmetic composition of claim 1, wherein the at least one coating layer has a thickness ranging from about 1 nm to about 50 nm.

3. The cosmetic composition of claim 1, wherein the at least one particulate titanium dioxide has a mean particle size ranging from about 1 nm to about 50 nm.

4. The cosmetic composition of claim 1, wherein the at least one small particle comprises a cross-linked styrene/methyl methacrylate copolymer.

5. The cosmetic composition of claim 1, wherein the at least one non-emulsifying organopolysiloxane elastomer is in the form of a gel or powder.

6. The cosmetic composition of claim 1, wherein the at least one porous oil absorbing agent is present in the composition in an amount ranging from about 1% to about 40% by weight, relative to the total weight of the composition.

7. The cosmetic composition of claim 1, wherein the at least one porous oil absorbing agent is chosen from silicas, polyamide powders, powders of acrylic polymers, perlites, magnesium carbonate, and mixtures thereof.

8. The cosmetic composition of claim 7, wherein the powders of acrylic polymers are chosen from powders of polymethyl methacrylate, powders of polymethyl methacrylate/ethylene glycol dimethacrylate, powders of polyallyl methacrylate/ethylene glycol dimethacrylate, or powders of ethylene glycol dimethacrylate/lauryl methacrylate copolymer.

9. The cosmetic composition of claim 1, wherein the cosmetic composition is in the form of a liquid, powder, or aerosol foam.

10. A method for improving at least one property chosen from UV filtration and/or pore hiding on the skin, said method comprising:
applying to the skin at least one layer of a cosmetic composition comprising:
(i) at least one composite pigment comprising:
(a) at least one small particle comprising a styrene/acrylate copolymer, wherein the at least one small particle is at least partially covered with at least one coating layer comprising at least one particulate titanium dioxide,
(b) at least one large particle comprising a polymethyl methacrylate polymer, and
(c) optionally at least one coloring pigment,
wherein the at least one small particle has a mean particle size ranging from about 100 nm to about 600 nm,
wherein the at least one large particle has a mean particle size of greater than about 2 µm,
wherein the weight ratio of the at least one small particles to the at least one large particle ranges from 50:50 to 90:10, and
wherein the composite pigment is obtained by a mechanochemical fusion process;
(ii) at least one non-emulsifying organopolysiloxane elastomer chosen from dimethicone crosspolymers, present in an amount ranging from about 8.3% to about 10% by weight relative to the total weight of the composition; and
(iii) at least one porous oil absorbing agent with an oil absorption capability of from 1 to 15 mL/g,
wherein the at least one porous oil absorbing agent is present in an amount greater than about 1% by weight, relative to the total weight of composition.

11. The method according to claim 10,
wherein the surface of the at least one large particle is optionally at least partially covered with at least one coating layer; and
wherein the at least one coating layer comprises at least one of particulate titanium dioxide or coloring pigments.

12. The cosmetic composition of claim 1, wherein the weight ratio of the at least one small particle to the at least one particulate titanium dioxide ranges from 30:70 to 70:30.

13. The cosmetic composition of claim 1, wherein the weight ratio of the at least one small particle to the at least one particulate titanium dioxide ranges from 30:70 to 70:30.

14. The cosmetic composition of claim 1, wherein the weight ratio of the at least one small core particle to the at least one large particle and to the at least one particulate titanium dioxide ranges from 35:15:50 to 15:35:50.

15. A cosmetic composition comprising:
(i) at least one composite pigment comprising:
at least one small particle chosen from polymethyl methacrylate particles, wherein the at least one small particle is at least partially covered with at least one coating layer comprising at least one particulate titanium dioxide;
at least one large particle chosen from polyamide particles; and
optionally at least one coloring pigment;
wherein the at least one small particle has a mean particle size ranging from about 100 nm to about 600 nm;
wherein the at least one large particle has a mean particle size of greater than about 2 µm;
wherein the weight ratio of the at least one small particle to the at least one large particle ranges from 50:50 to 90:10; and
wherein the composite pigment is obtained by a mechanochemical fusion process;
(ii) at least one non-emulsifying organopolysiloxane elastomer chosen from dimethicone crosspolymers, present in an amount ranging from about 8.3% to about 10% by weight relative to the total weight of the composition; and
(iii) at least one porous oil absorbing agent with an oil absorption capability of from 1 to 15 mL/g, wherein the at least one porous oil absorbing agent is present in an amount greater than about 1% by weight, relative to the total weight of composition.

* * * * *